(12) United States Patent
Moore

(10) Patent No.: US 12,376,976 B1
(45) Date of Patent: Aug. 5, 2025

(54) PROSTHETIC SOCKET

(71) Applicant: Zachary Charles Moore, Albion, NY (US)

(72) Inventor: Zachary Charles Moore, Albion, NY (US)

(*) Notice: Subject to any disclaimer, the term of this patent is extended or adjusted under 35 U.S.C. 154(b) by 0 days.

(21) Appl. No.: 19/173,740

(22) Filed: Apr. 8, 2025

(51) Int. Cl.
*A61F 2/80* (2006.01)
*A61F 2/66* (2006.01)
*A61F 2/60* (2006.01)

(52) U.S. Cl.
CPC .............. *A61F 2/80* (2013.01); *A61F 2/66* (2013.01); *A61F 2002/607* (2013.01)

(58) Field of Classification Search
CPC . A61F 2/80; A61F 2002/607; A61F 2002/608
See application file for complete search history.

(56) References Cited

U.S. PATENT DOCUMENTS

| | | | | |
|---|---|---|---|---|
| 1,144,681 | A * | 6/1915 | Apgar | A61F 2/601 623/47 |
| 2,506,464 | A * | 5/1950 | Millheisler | A61F 13/105 602/22 |
| 2003/0023324 | A1 * | 1/2003 | Laghi | A61F 2/78 623/36 |
| 2014/0135946 | A1 * | 5/2014 | Hurley | A61F 2/5044 623/33 |
| 2016/0158035 | A1 * | 6/2016 | Alley | A61F 2/80 623/33 |

* cited by examiner

*Primary Examiner* — Bruce E Snow
(74) *Attorney, Agent, or Firm* — Jong Patent Firm; Cheng Ning Jong; Tracy P. Jong

(57) ABSTRACT

A prosthetic socket includes multiple panels supported by a first base with a rotational axis and support members. An adjustment disk, co-axially aligned with the base, features an actuator coupled to the support members. Rotating the adjustment disk in one direction moves the panels closer to the axis, reducing the socket opening. Rotating it in the opposite direction increases the opening by moving the panels farther from the axis.

18 Claims, 21 Drawing Sheets

PROSTHETIC SOCKET

BACKGROUND OF THE INVENTION

1. The Field of the Invention

The present invention relates to an adjustable prosthetic socket. More specifically, the present invention is directed to an adjustable prosthetic socket adjustable by means of a rotational adjustment mechanism.

2. Background Art

Prosthetic sockets serve as the critical interface between a residual limb and a prosthesis. While advancements in materials and design have improved functionality, significant challenges persist. Poorly fitted sockets can cause discomfort, pressure points, and skin irritation, leading to pain, blisters, or pressure sores. Hard materials may not conform well to the limb, reducing comfort during prolonged use, while uneven pressure distribution can cause tissue damage. Lack of breathability may result in excessive sweating, skin irritation, and odor. Additionally, some users experience allergic reactions to materials such as silicone or thermoplastics, and friction between the skin and socket can lead to abrasions.

Many sockets are designed for a fixed shape, failing to accommodate residual limb fluctuations due to weight changes, swelling, or muscle atrophy. Adjustments often require visits to a prosthetist, adding inconvenience and cost. Durability concerns also exist. For instance, frequent use can lead to wear and tear, while weaker materials may crack under stress. Weight and bulkiness are further drawbacks, as heavier sockets increase fatigue, and large designs may interfere with clothing or mobility. Custom sockets can be expensive, and financial barriers limit access to frequent replacements or adjustments. Moreover, many sockets are designed for specific activities, requiring users to switch prostheses, while some are incompatible with advanced prosthetic components, restricting functionality.

Psychological and social factors also play a role, as bulky or visible sockets may cause self-consciousness. Adaptation challenges can lead to frustration or dissatisfaction. Maintenance difficulties, including hygiene concerns and frequent upkeep, add to user burden.

There is a growing demand for prosthetic devices that users can independently don and doff without external assistance. Even with custom fitting, an adjustable socket would provide significant benefits by allowing users to easily modify its size, e.g., tightening or enlarging the opening to facilitate stump insertion and ensure a secure, comfortable fit. Addressing these issues requires innovation in socket design, such as advanced materials, dynamic fit systems, and enhanced customization options.

SUMMARY OF THE INVENTION

In accordance with the present invention, there is provided a prosthetic socket including:
(a) a plurality of panels;
(b) a first base including a first rotational axis and a plurality of support members disposed about the first rotational axis, wherein each of the plurality of panels is supported by a corresponding support member of the plurality of support members to define a socket opening; and
(c) an adjustment disk including a second rotational axis and an actuator, wherein the second rotational axis is co-axially aligned with the first rotational axis, and the actuator is functionally coupled to the plurality of support members,
wherein a rotation of the adjustment disk in a first direction relative to the first base moves each of the plurality of panels to a first position, reducing their perpendicular distance from the first rotational axis and decreasing the socket opening and a rotation of the adjustment disk in a second, opposite direction moves each of the plurality of panels to a second position, increasing their perpendicular distance from the first rotational axis and enlarging the socket opening.

In one embodiment, the actuator includes a cam. In one embodiment, the plurality of support members are four support members. In one embodiment, the prosthetic socket further includes a lock configured to be applicable to releasably immobilize the plurality of support members with respect to the actuator in a position ranging from the first position to the second position. In one embodiment, a lengthwise cross-section of at least one of the plurality of support members is a polygon.

In accordance with the present invention, there is further provided a prosthetic socket including:
(a) a plurality of panels;
(b) a plurality of support members, each configured to support one of the plurality of panels;
(c) a base including a first base and an adjustment disk disposed adjacent to the first base, wherein the first base includes a first rotational axis and a plurality of channels arranged about the first rotational axis, and the adjustment disk includes a second rotational axis co-axially aligned with the first rotational axis and a plurality of slots arranged about the second rotational axis;
(d) at least one selective locking mechanism attached to one of the plurality of support members, the at least one selective locking mechanism configured to be disposed in one of an on state and an off state, within a plane perpendicular to the first rotational axis; and
(e) an outer ring including a central plane and at least one lock-releasing mechanism, the at least one lock-releasing mechanism being functionally coupled to the at least one selective locking mechanism to enable its release, wherein the outer ring is disposed such that the central plane is substantially coplanar with the plane of the at least one selective locking mechanism,
wherein each of the plurality of support members is positioned within a corresponding channel, and each of the at least one selective locking mechanism is slidably engaged with a corresponding slot of the plurality of slots such that the plurality of panels form an opening for receiving a patient's residual limb, a rotation of the adjustment disk about the first rotational axis in a first direction enlarges the opening to accommodate the patient's residual limb, a rotation of the adjustment disk in an opposite, second direction reduces the opening, bringing the plurality of panels into contact with the patient's residual limb and the at least one selective locking mechanism is placed in the on state to immobilize the plurality of panels around the patient's residual limb, and a rotation of the outer ring activates the at least one lock-releasing mechanism, transitioning the at least one selective locking mechanism to the off state, allowing adjustment of the opening.

In one embodiment, the at least one selective locking mechanism and the plurality of slots together include a rachet. In one embodiment, the rachet includes a pawl configured to be engaged with a plurality of teeth disposed along a periphery of one of the plurality of slots. In one embodiment, the at least one selective locking mechanism includes a first magnet, the at least one lock-releasing mechanism includes a second magnet and the second magnet is configured to interact with the first magnet to dispose the at least one selective locking mechanism in an off-state from an on-state. In one embodiment, the prosthetic socket further includes a second base configured to be removably coupled with the first base, wherein the adjustment disk is disposed between the first base and the second base. In one embodiment, the prosthetic socket further includes a pin lock system for releasably securing a pin of a liner disposed over the patient's residual limb. In one embodiment, a lengthwise cross-section of at least one of the plurality of support members is a polygon. In one embodiment, the plurality of support members are four support members.

An object of the present invention is to provide a prosthesis having a socket that is adjustable in size.

Another object of the present invention is to provide a prosthesis having a socket that is easily adjustable in size with simple actions of the patient.

Another object of the present invention is to provide a prosthesis having a socket that is easily adjustable in size with simple actions of the patient using only one hand.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

PARTS LIST

Figure 1:
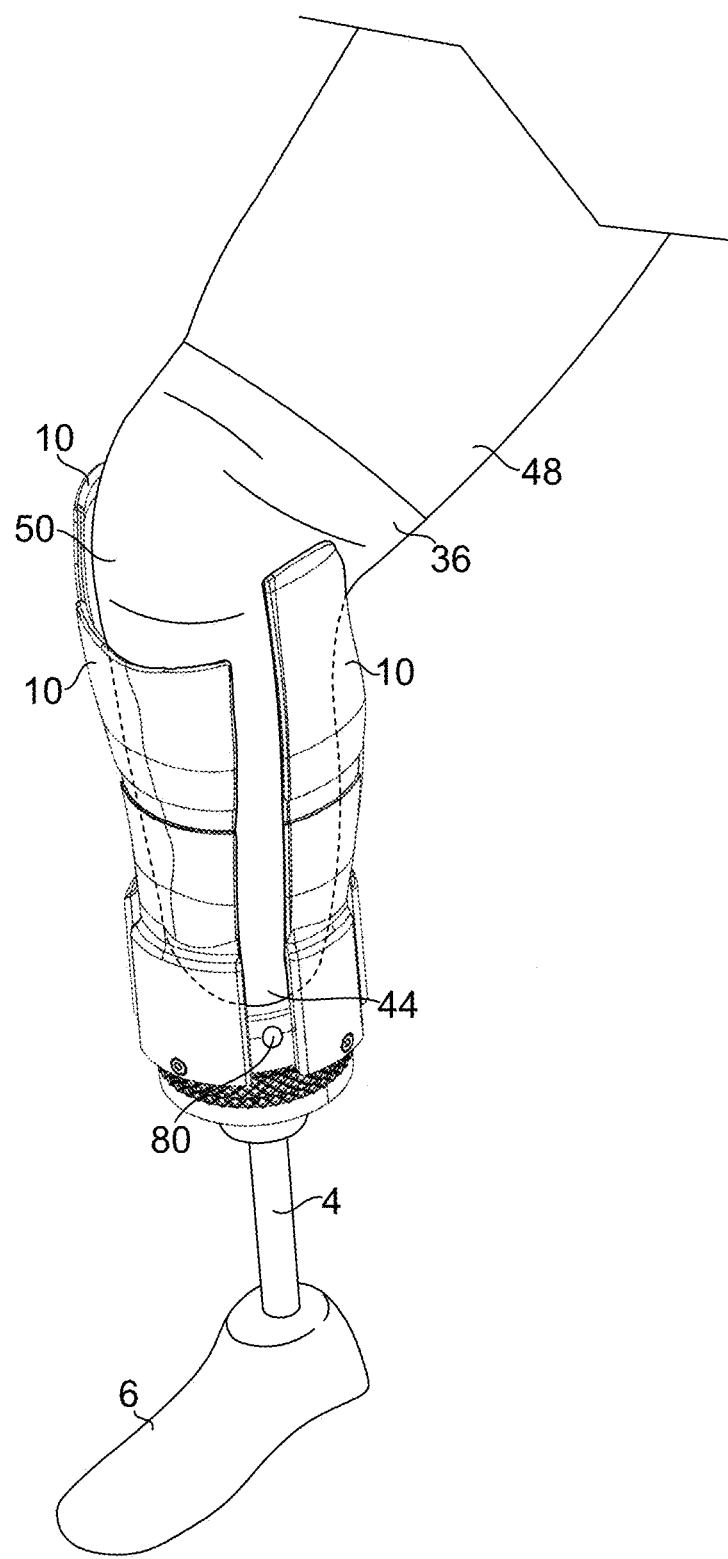
FIG. 1 is a diagram depicting a prosthetic leg utilizing a present prosthetic socket having been fitted to a residual limb of a patient.

2—prosthesis
4—pylon

6—prosthetic leg
8—prosthetic socket
10—panel
12—first base
14—second base
16—stop ring
18—channel
20—fastener
22—upper portion of panel
24—bottom portion of panel
26—grip surface
28—pin lock system
30—spring
32—pin
34—slot
36—prosthetic liner
38—through hole
40—adjustment disk
42—outer ring
44—residual limb
46—support member
48—patient's thigh
50—patient's knee
52—selective locking mechanism
54—recess
56—strap
58—hook portion
60—loop portion
62—teeth
64—pawl
66—spring
68—magnet
70—magnet
72—outer periphery
74—frame
76—tapered edge
78—opening of frame
80—push pin
82—direction of applied force
84—rotational axis of first base
86—rotational axis of adjustment disk
88—connector
90—plane upon which slots are disposed
92—spring stop
94—hook
96—ring
98—plate
100—housing
102—sleeve
104—knob
106—divot
108—actuator
110—cam

PARTICULAR ADVANTAGES OF THE INVENTION

The present prosthetic socket is configured to be adjustable such that the volume or opening encompassed by the outer periphery of the socket is adjustable along the entire depth of the volume or opening. Therefore, when the socket is tightened around a patient's residual limb, the socket is tightened around the patient's limb with uniform pressure. In contrast, in a prior art prosthetic socket, a periphery of the socket is tightened around the limb, unnecessarily compressing the skin, subcutaneous tissue, and underlying muscles, which can cause discomfort or pain if excessive. Prolonged or intense compression can irritate or compress nerves, leading to tingling, numbness, or pain, e.g., nerve impingement or neuropathy. However, if not tightened around the limb sufficiently tightly, the socket can easily detach and fail to provide sufficient support to the patient.

The present prosthetic socket can be adjusted using a twist action applied to the base of the prosthetic socket to result in a desired opening of the prosthetic socket, providing an easy-to-use mechanism capable of yielding a suitable socket size for comfortably receiving a patient's residual limb covered in a prosthetic liner. For instance, as long as the socket is immobilized, e.g., by pinching the socket between one's arm and another body part, the patient may adjust the opening size of the socket using only one hand even before the socket has been disposed over the patient's residual limb. Further, the socket may also be tightened against the patient's residual limb after the socket has been placed around the patient's residual limb by simply twisting a lower base portion against an upper base portion connected to the socket. If loosening of the socket is desired, a ring disposed around or on an outer surface of the base can be rotated, allowing the socket to be loosened and detached with little effort.

Some prior art prostheses are vacuum-secured prostheses. A vacuum-secured prosthesis is a prosthetic limb that uses a vacuum pump to create negative pressure between the socket and the residual limb. This suction keeps the limb secure and stable, and can help improve circulation and comfort. A vacuum pump is attached to the socket. The pump evacuates air from the socket, creating negative pressure. The liner and residual limb are pulled into the socket wall. The vacuum maintains negative pressure regardless of limb movement. The vacuum reduces limb movement and distributes pressure evenly. Such prostheses require more a time-consuming procedure for properly fitting and aligning vacuum-sealed prostheses compared to a prosthesis with a present prosthetic socket and other suspension systems. A vacuum-secured prosthesis requires regular cleaning and maintenance to ensure proper vacuum seal and function. Any failure in the seal can compromise suspension. Vacuum-secured systems are generally more expensive than other types of prosthetic suspension systems and a prosthesis with a present prosthetic socket.

Further, as the present socket affords adjustability of the socket opening, no additional socks are needed to fill out one's residual limb, e.g., by sliding one or more socks over the residual limb, such that the residual limb may be fitted more snuggly in a conventional pin lock suspension system.

DETAILED DESCRIPTION OF A PREFERRED EMBODIMENT

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Figure 2:
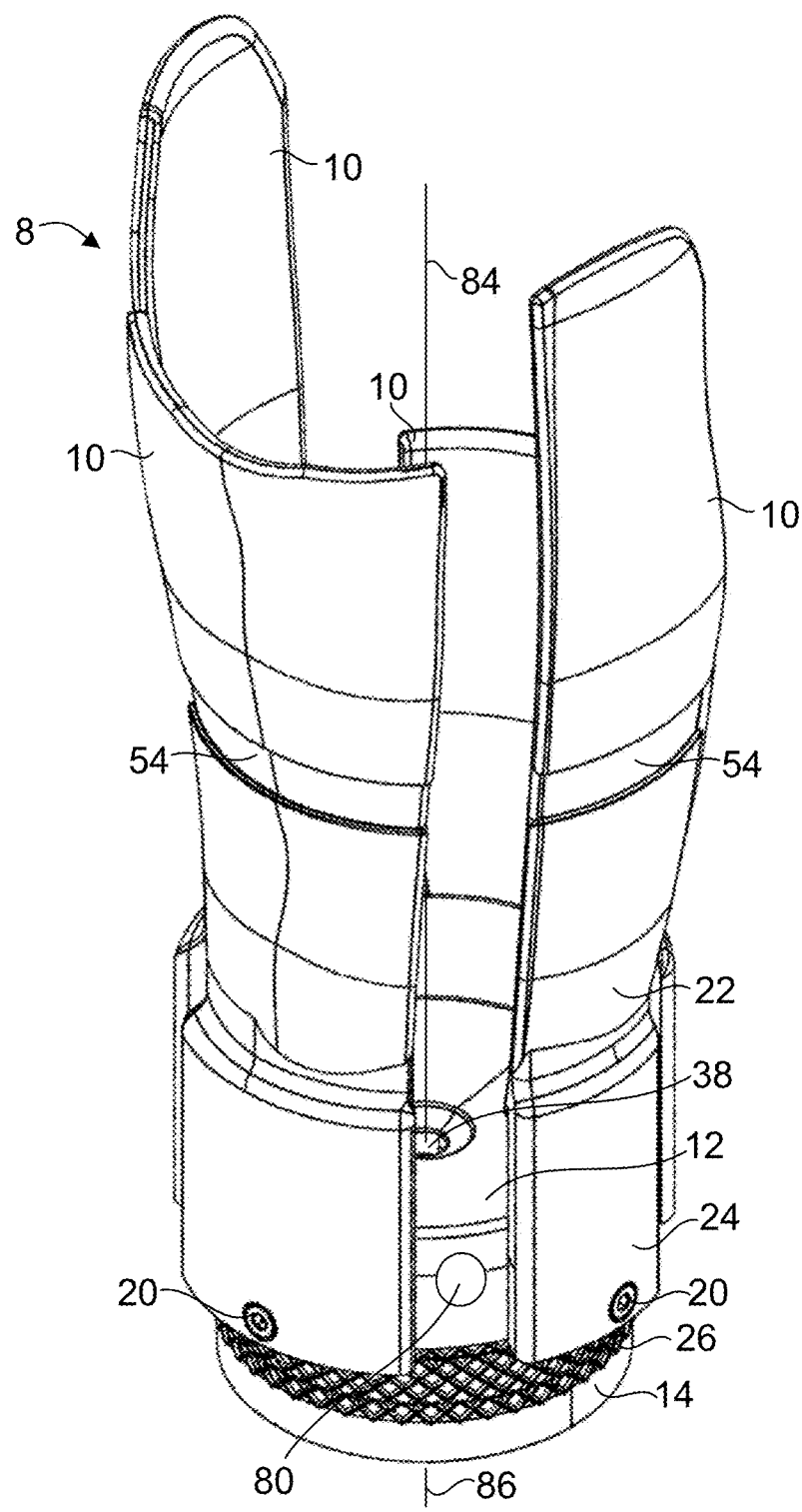
FIG. 2 is a top perspective view of a present prosthetic socket.
Figure 3:
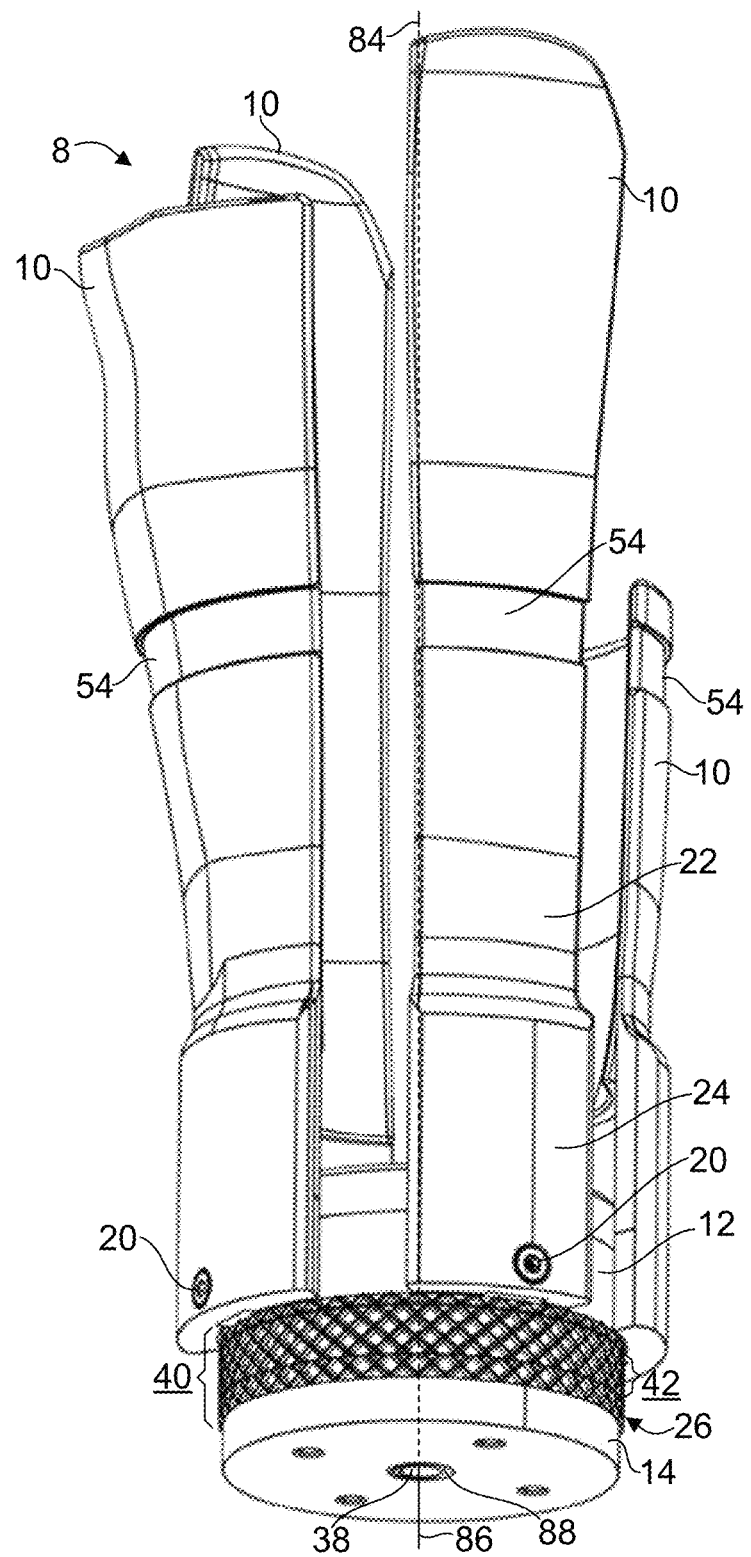
FIG. 3 is a bottom perspective view of a present prosthetic socket.
Figure 4:
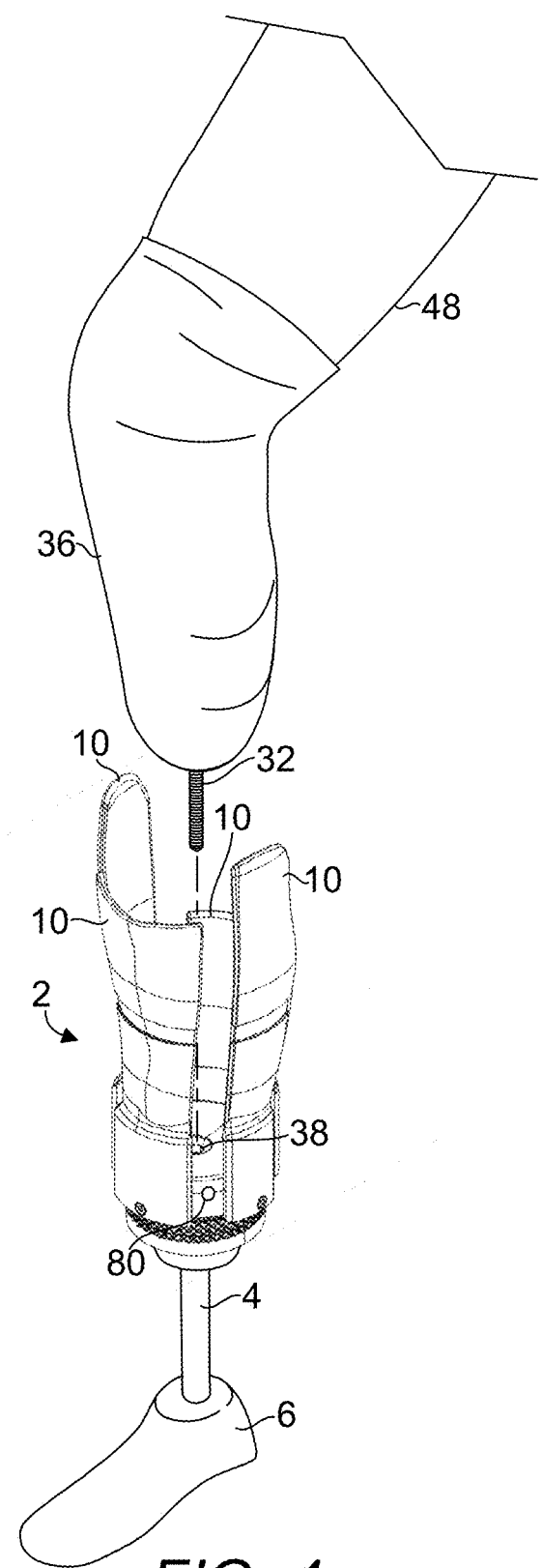
FIG. 4 is a diagram depicting a prosthetic leg utilizing a present prosthetic socket aligned to receive a patient's residual limb covered with a prosthetic liner.
Figure 5:
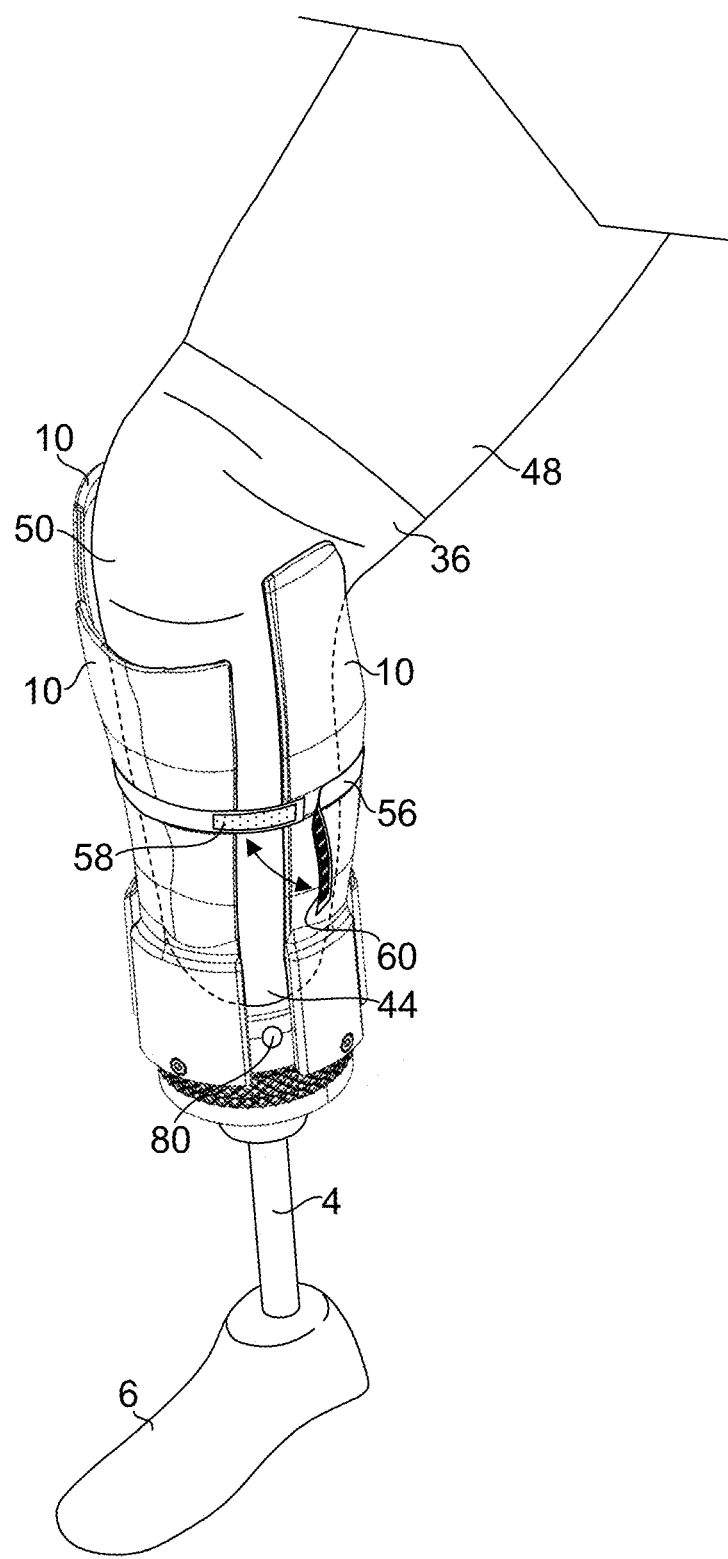
FIG. 5 is a diagram depicting a prosthetic leg utilizing a present prosthetic socket having been fitted to a residual limb of a patient and a strap utilized to further secure the present panels of the present prosthetic socket to the residual limb.

FIG. 1 is a diagram depicting a prosthetic leg 6 utilizing a present prosthetic socket 8 having been fitted to a residual limb of a patient. FIG. 2 is a top perspective view of a present prosthetic socket 8. FIG. 3 is a bottom perspective view of a present prosthetic socket 8. FIG. 4 is a diagram depicting a prosthetic leg 6 utilizing a present prosthetic socket 8 aligned to receive a patient's residual limb covered with a prosthetic liner 36. FIG. 5 is a diagram depicting a prosthetic leg 6 utilizing a present prosthetic socket 8 having been fitted to a residual limb of a patient and a strap 56 utilized to further secure the present panels 10 of the present prosthetic socket to the residual limb 44. The upper portion 22 of a panel 10 is primarily shaped to accommodate a patient's residual limb 44 while the lower portion 24 of the panel 10 is secured to a support member 46 using, e.g., a fastener 20. In the examples shown throughout, the prosthesis is useful for extending the patient's leg below the patient's knee 50 as the lower limb has been amputated. Although not shown, the present prosthetic socket is also suitable to be adapted to a residual limb of another type, e.g., a residual limb on an upper leg or an arm. The prosthetic socket 8 includes a plurality of panels 10, a first base 12 and an adjustment disk 40. The first base 12 includes a first rotational axis 84 and a plurality of support members 46 disposed about the first rotational axis 84. Each of the panels 10 is configured to be supported by one of the support members 46. The adjustment disk 40 includes a second rotational axis 86 and an actuator 108. The second rotational axis 86 is co-axially disposed with the first rotational axis 84. The actuator 108 is configured to be functionally coupled to the plurality of support members 46 such that a first rotation of the adjustment disk 40 with respect to the first base 12 in a first direction causes each of the plurality of panels 10 to be disposed at a smaller perpendicular distance, in a first position, from the first rotational axis 84 to provide a smaller opening of the socket and a second rotation of the adjustment disk 40 with respect to the first base in a second, opposite direction causes each of the plurality of panels 10 to be disposed at a larger perpendicular distance, in a second position, from the first rotational axis 84 to provide a larger opening of the socket. Recesses 54 are integrated into the panels 10, allowing a strap 56, with hook and loop portions 58, 60 at its ends, to be applied along the recesses 54 after the prosthesis is fitted onto the residual limb 44. This enhances the tightening and securing of the panels 10 against the residual limb 44. Grip surfaces 26, e.g., knurled surfaces, etc., facilitate the adjustment of the adjustment disk 40 relative to the first base 12 and serve as indicators for the locations of the adjustment disk 40 and the outer ring 42. The lengthwise cross-section of a support member is preferably a polygon, such as a rectangle, rather than a circle, to prevent rotation about its lengthwise axis within a correspondingly shaped channel.

In the embodiment shown throughout, Applicant discovered that four support members 10 render adequate support as a prosthetic socket while providing sufficient flexibility at the opening of the socket to receive a patient's residual limb 44. Although additional support members may enhance flexibility of the prosthetic socket to receive a residual limb, the increase in the number of support members may unnecessarily complicate the prosthetic socket and dramatically increase the parts count of the prosthetic socket. Two opposingly disposed panels may suffice although there may not be sufficient adjustments that can be made to the prosthetic socket formed of just two panels.

Figure 6:
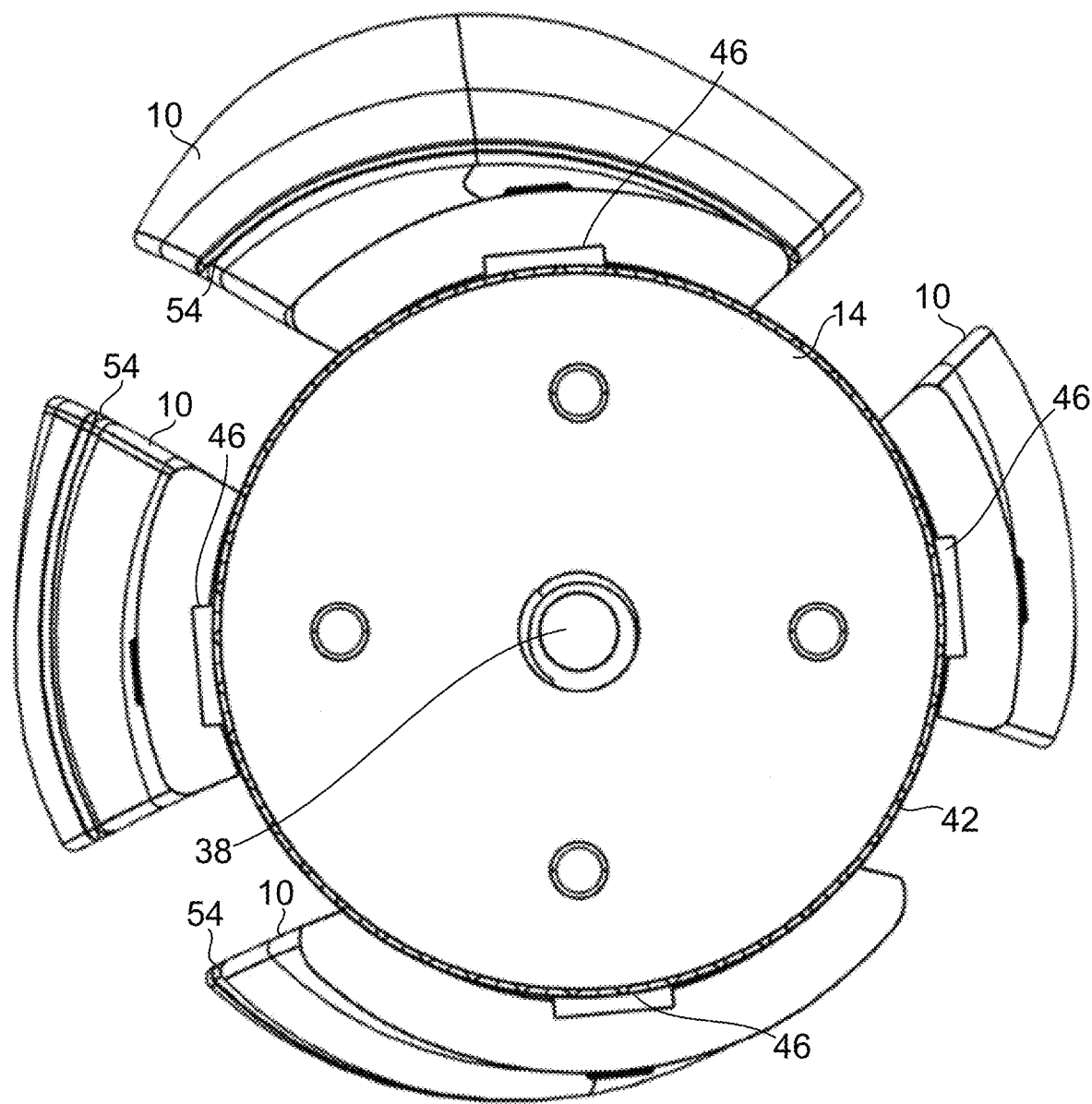
FIG. 6 is a bottom perspective view of a present prosthetic socket disposed in a retracted state.
Figure 7:
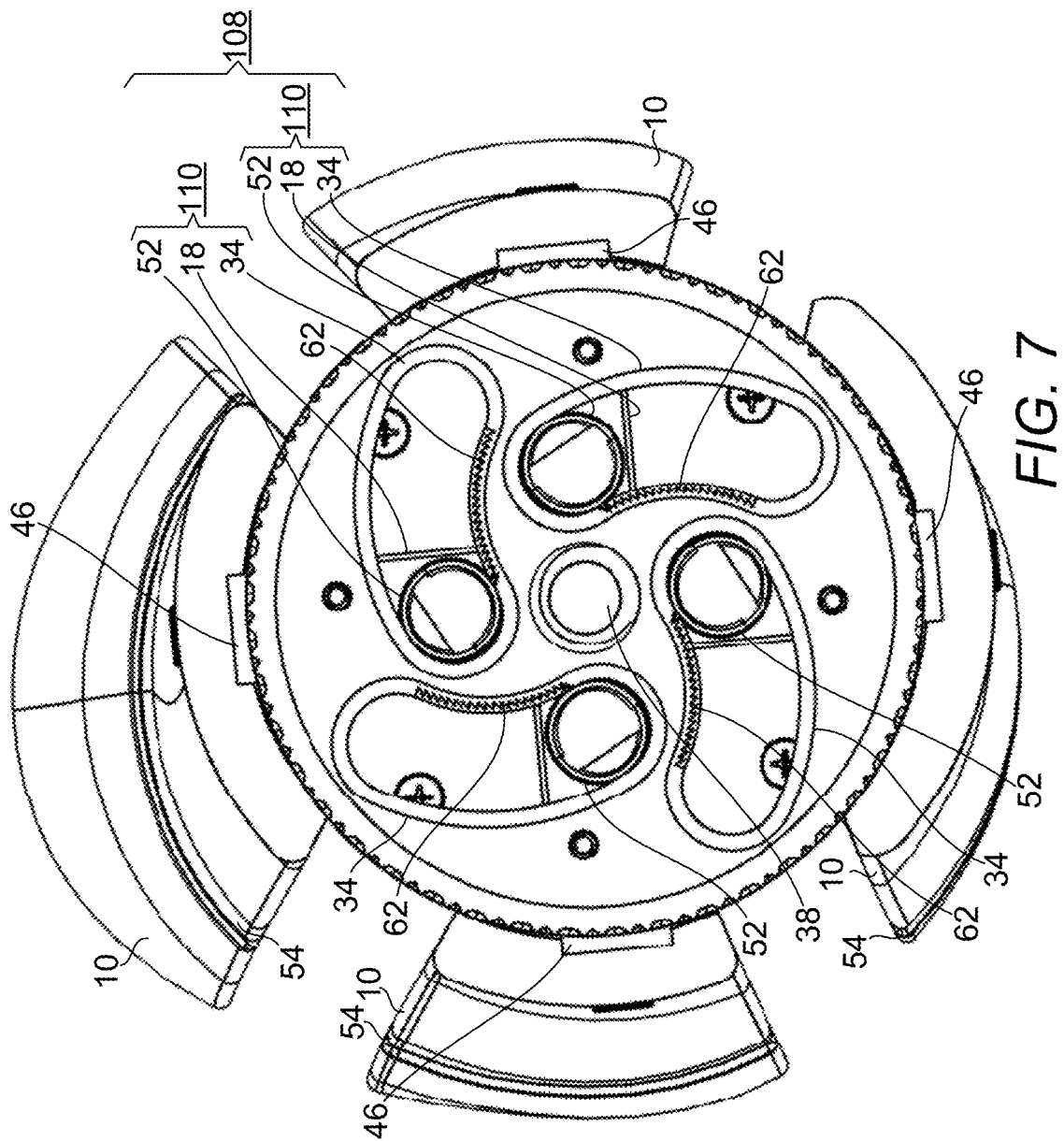
FIG. 7 is a bottom view of a present prosthetic socket disposed in a retracted state, with a bottom plate of the adjustment disk and the second base removed to reveal a mechanism useful for expanding or minimizing the socket size.
Figure 8:
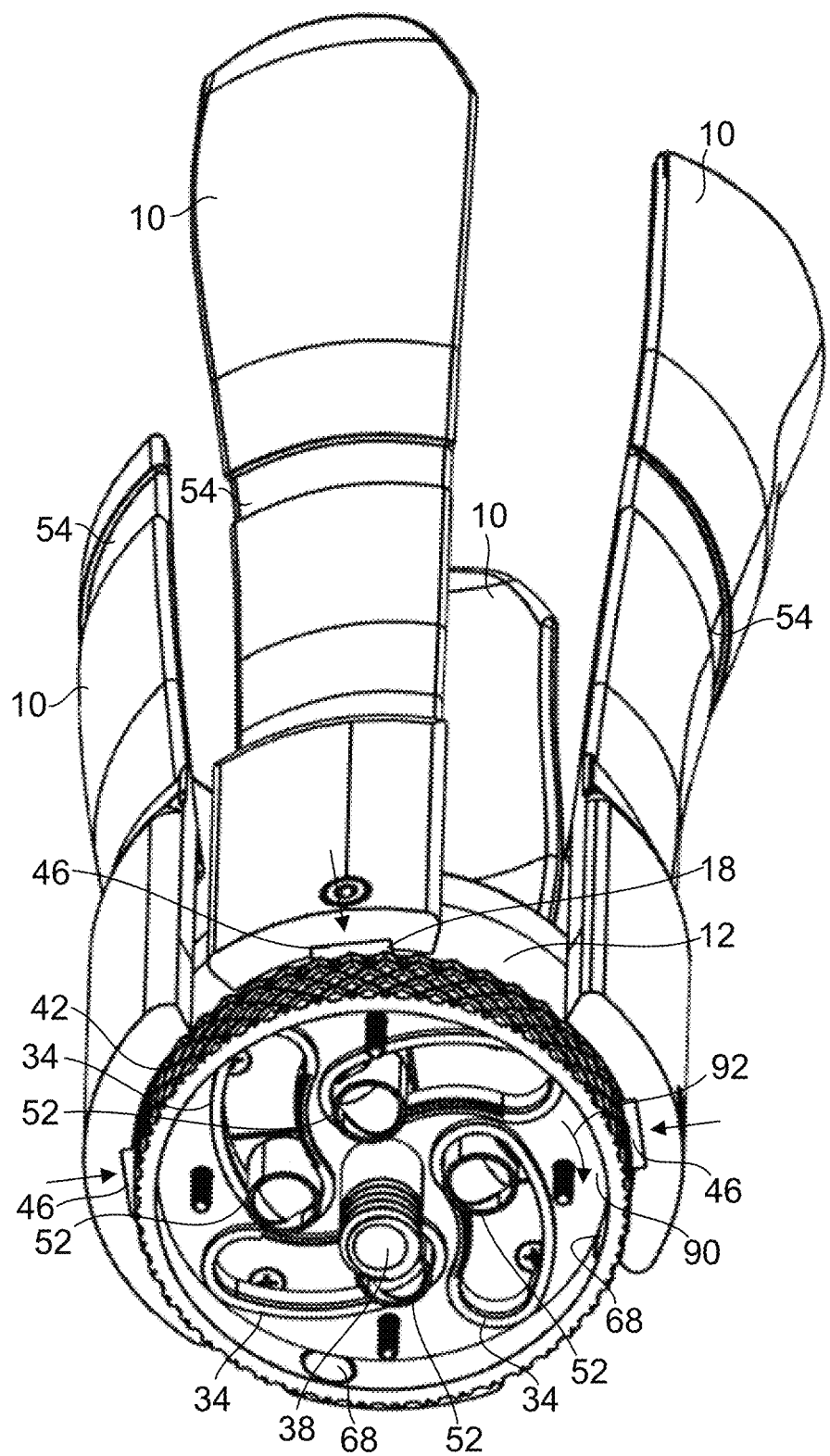
FIG. 8 is a bottom perspective view of a present prosthetic socket disposed in a retracted state, with a bottom plate of the adjustment disk and the second base removed to reveal a mechanism useful for expanding or minimizing the socket size.
Figure 9:
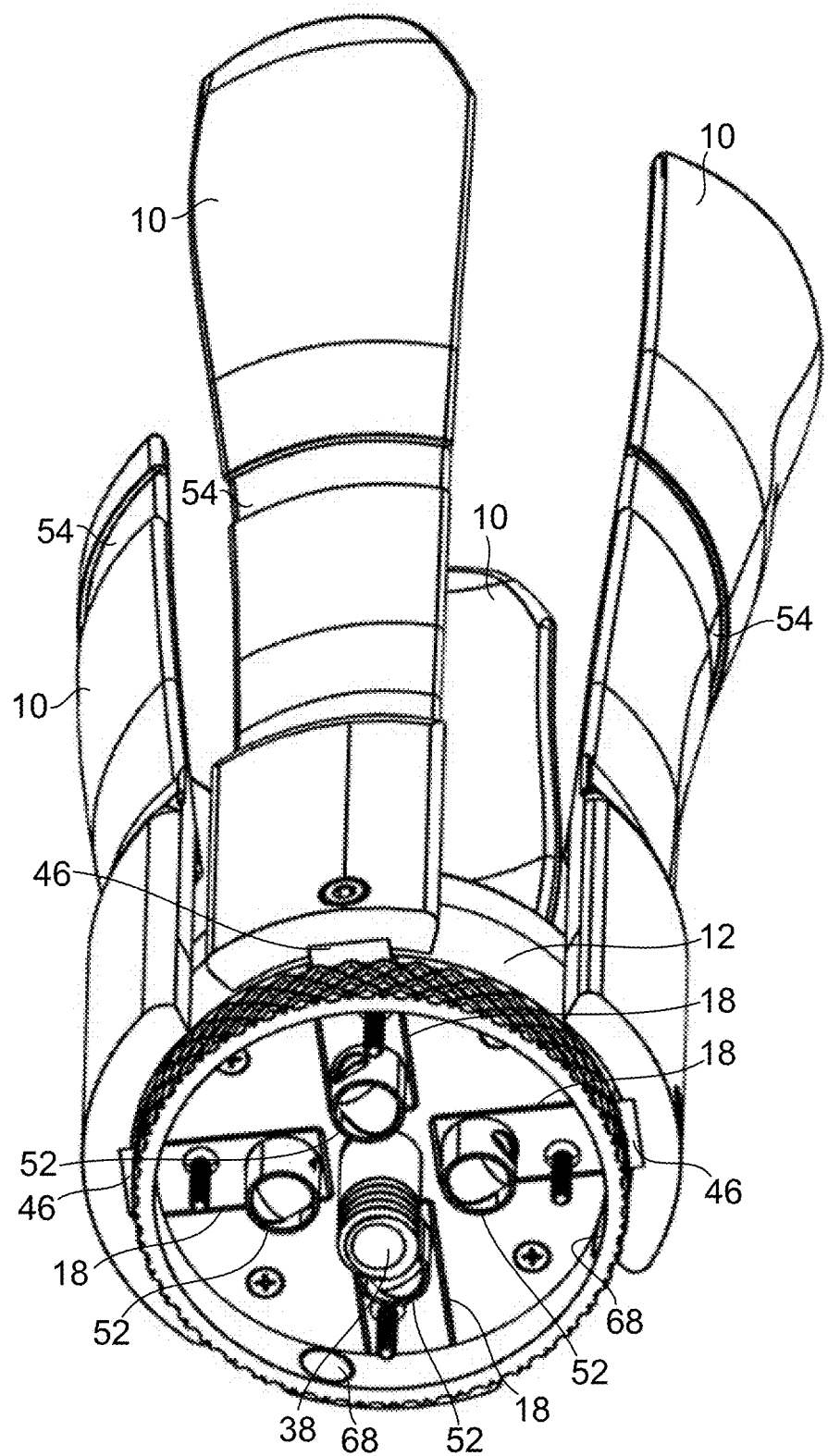
FIG. 9 depicts a present prosthetic socket shown in FIG. 8 with a top plate of the adjustment disk and second base also removed to further reveal a mechanism useful for expanding or minimizing the socket size.
Figure 10:
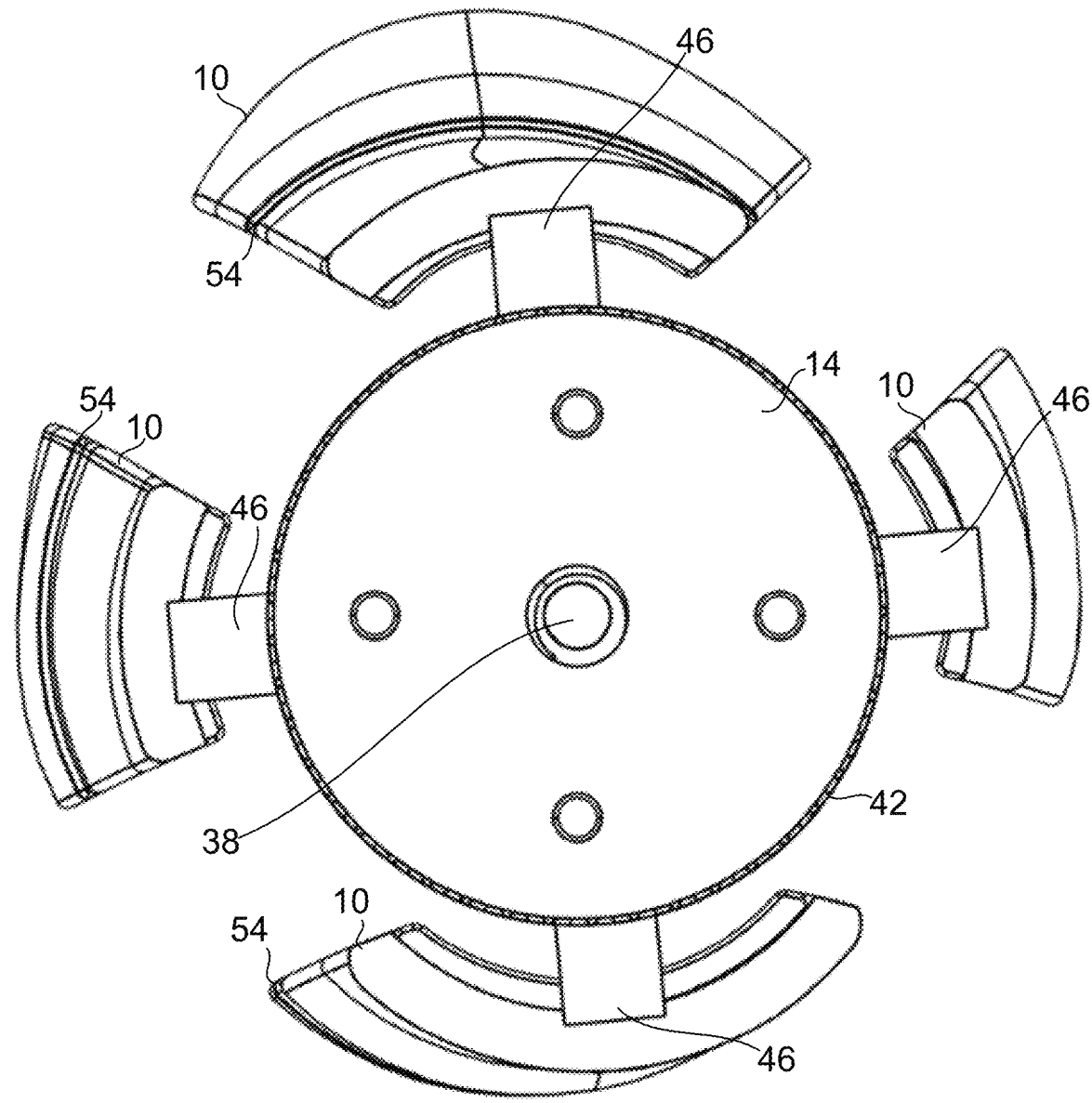
FIG. 10 is a bottom perspective view of a present prosthetic socket, disposed in an expanded state.
Figure 11:
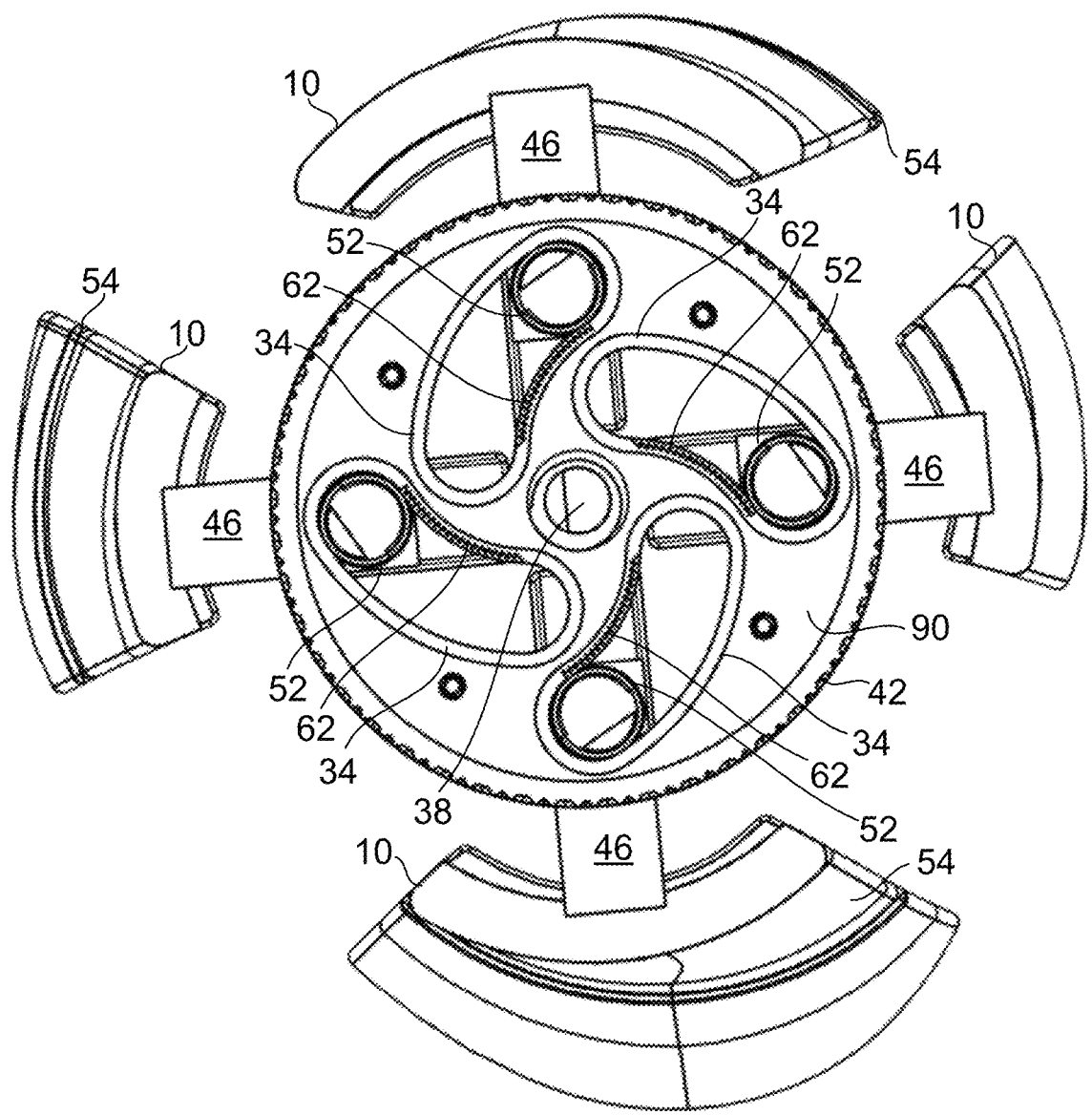
FIG. 11 is a bottom view of a present prosthetic socket disposed in an expanded state, with a bottom plate of the adjustment disk and the second base removed to reveal a mechanism useful for expanding or minimizing the socket size.
Figure 12:
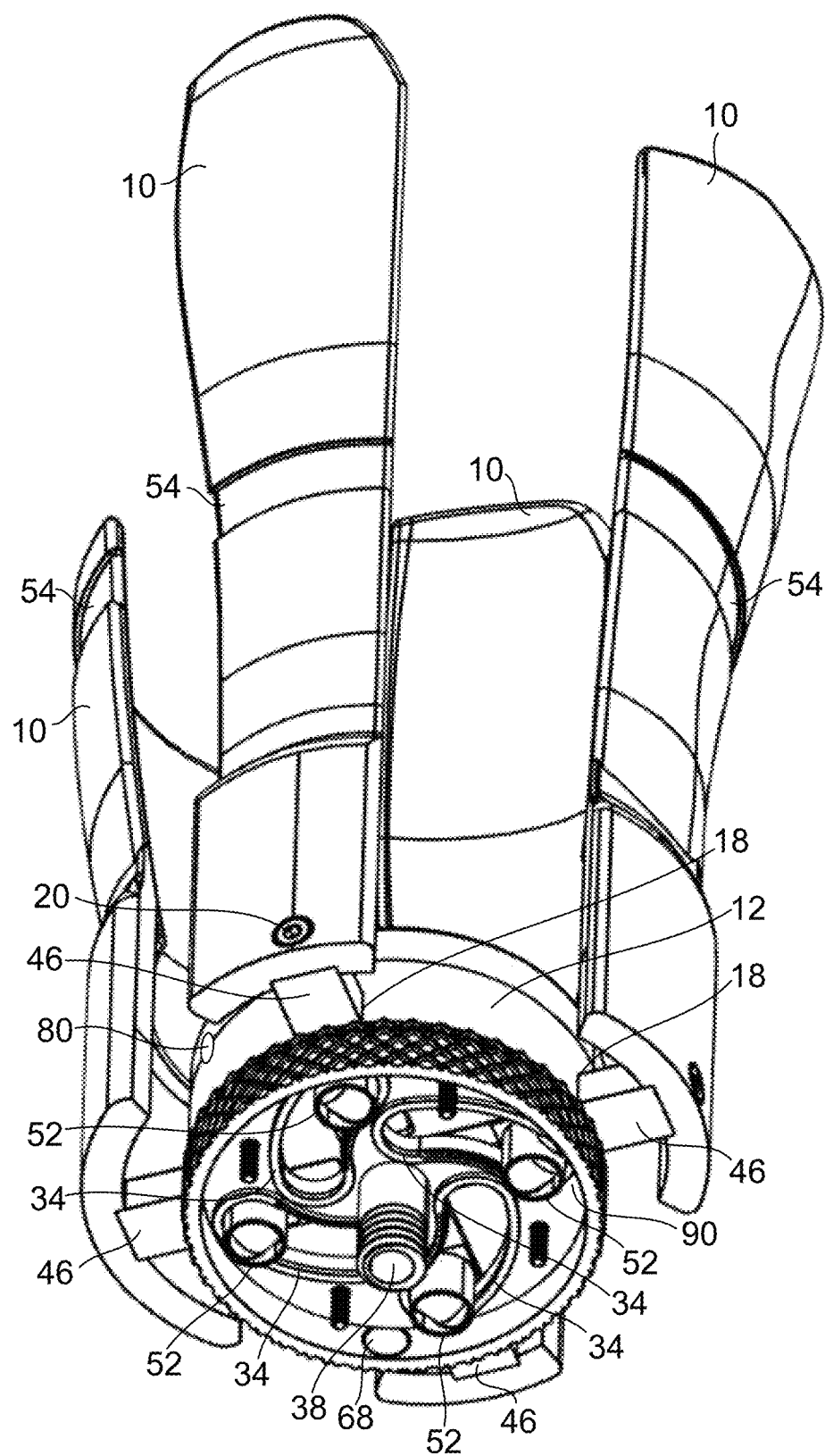
FIG. 12 is a bottom perspective view of a present prosthetic socket disposed in an expanded state, with a bottom plate of the adjustment disk and the second base removed to reveal a mechanism useful for expanding or minimizing the socket size.
Figure 13:
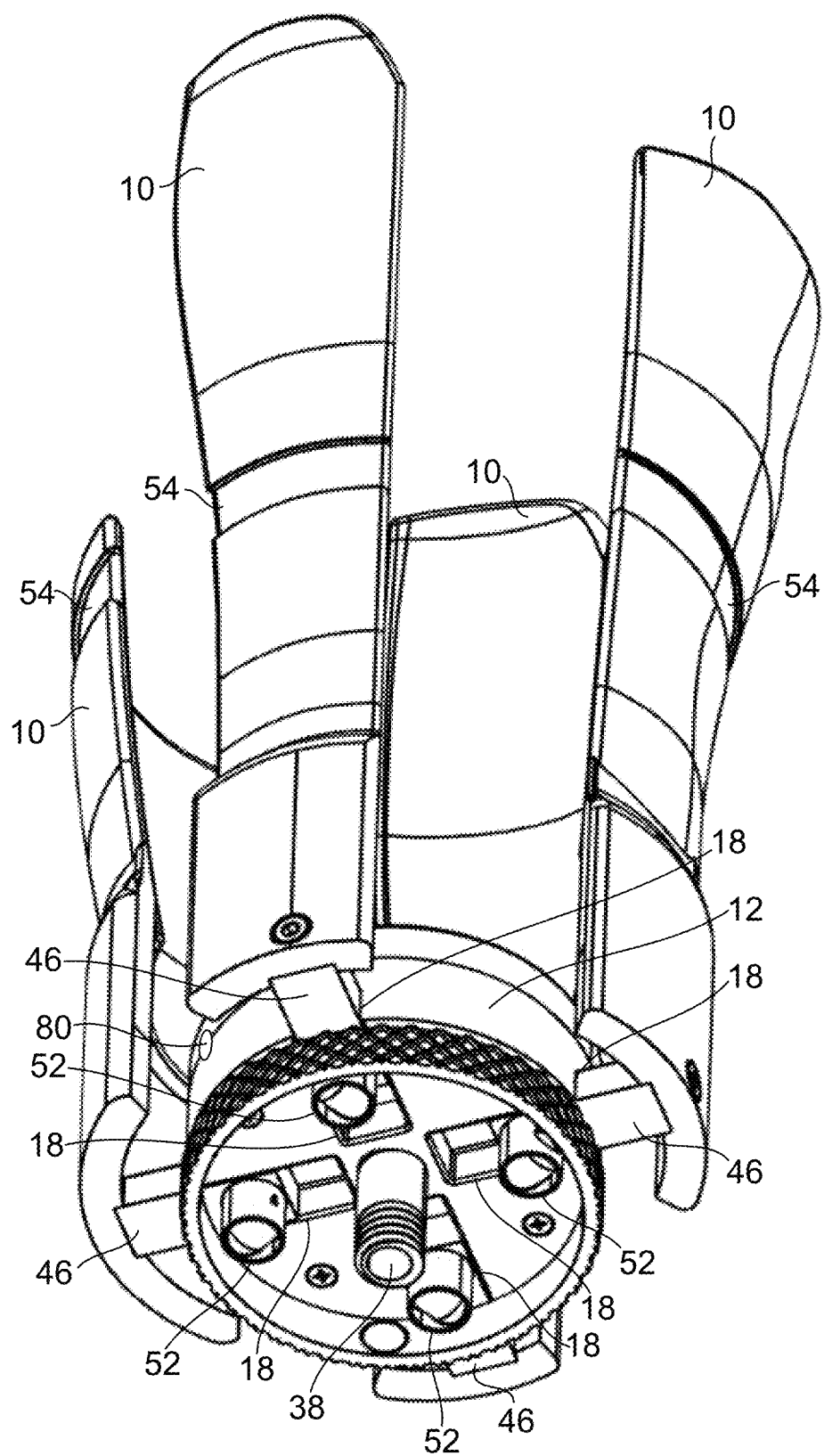
FIG. 13 depicts a present prosthetic socket shown in FIG. 12 with a top plate of the adjustment disk and second base also removed to further reveal a mechanism useful for expanding or minimizing the socket size.

FIG. 6 is a bottom perspective view of a present prosthetic socket disposed in a retracted state. FIG. 7 is a bottom view of a present prosthetic socket disposed in a retracted state, with a bottom plate of the adjustment disk and the second base removed to reveal a mechanism useful for expanding or minimizing the socket size. FIG. 8 is a bottom perspective view of a present prosthetic socket disposed in a retracted state, with a bottom plate of the adjustment disk and the second base removed to reveal a mechanism useful for expanding or minimizing the socket size. FIG. 9 depicts a present prosthetic socket shown in FIG. 8 with a top plate of the adjustment disk and second base also removed to further reveal a mechanism useful for expanding or minimizing the socket size. It shall be noted that the support members 46 are fully retracted in the state shown. FIG. 10 is a bottom perspective view of a present prosthetic socket, disposed in an expanded state. FIG. 11 is a bottom view of a present prosthetic socket disposed in an expanded state, with a bottom plate of the adjustment disk and the second base removed to reveal a mechanism useful for expanding or minimizing the socket size. FIG. 12 is a bottom perspective view of a present prosthetic socket disposed in an expanded state, with a bottom plate of the adjustment disk and the second base removed to reveal a mechanism useful for expanding or minimizing the socket size. FIG. 13 depicts a present prosthetic socket shown in FIG. 12 with a top plate of the adjustment disk and second base also removed to further reveal a mechanism useful for expanding or minimizing the socket size. It shall be noted that the support members 46 are fully extended in the state shown.

In the embodiment shown throughout, the actuator 108 includes a plurality of cams 110, each configured to drive a support member 46 configured to be slidable with respect to a channel 18 disposed in the base. It shall be noted that each cam 110 is configured to drive a support member 46 having its motion confined within a channel 18, a selective locking mechanism 52 which extends from one end of the support member 46 into a slot 34 where the selective locking mechanism 52 is disposed in a sliding relationship with the slot 34. A plurality of slots 34 are disposed in a plane 90 such that a rotation of this plane causes the selective locking mechanisms 52 and hence the support members 46 to move along their respective channels, extending from the first base 12 or retracting into the first base 12. As the panels 10 are each attached to a support member 46, a rotation of the adjustment disk 40 relative to the first base 12 causes the opening defined by the panels 10 to enlarge or minimize. As the plane 90 is part of the adjustment disk 40, a rotation of the adjustment disk 40 about the second rotational axis 86 with respect to the first base 12 causes a movement of each selective locking mechanism 52 with respect to its corresponding slot 34 to which it is coupled. Referring to FIG. 8, a clockwise rotation 92 causes the support members 46 to be retracted as the slots 34 are arranged in a manner such that the parts of the slots coming into contact with the selective locking mechanisms 52, become closer to the center of the plane 90, urging the support members 46 closer to the center of the plane 90.

Referring to FIGS. 1-13, the base of the prosthetic socket includes a first base 12 and an adjustment disk 40 disposed adjacent the first base 12. The first base 12 includes a first rotational axis 84 and a plurality of channels 18 disposed about the first rotational axis 84. The adjustment disk 40 includes a second rotational axis 86 co-axially disposed with the first rotational axis 84 and a plurality of slots 34 disposed about the second rotational axis 86. Although in the embodiment shown throughout herein, each slot 34 is coupled with a selective locking mechanism 52, only one such locking mechanism 52 is required for a prosthetic socket, although less desirably so. When each slot 34 is paired with a selective locking mechanism 52 disposed in an on state, the prosthetic socket can receive the patient's residual limb more securely. Each selective locking mechanism 52 is configured to be attached to a support member 46 and disposed in a plane that is disposed at a right angle to the first rotational axis 84. The adjustment disk 40 further includes an outer ring 42 including a central plane and a plurality of lock releasing mechanisms, e.g., magnets 68 each functionally coupled with a selective locking mechanism 52. The outer ring 42 is disposed with the central plane substantially coplanar with the plane 90.

Before fitting a patient's residual limb in a prosthesis, the patient first dresses the residual limb 44 in a prosthetic liner 36. The prosthetic socket 8 is then adjusted to a size suitable to be fitted over the residual limb 44 if it is not already disposed in a suitable size. In putting on the prosthesis, the prosthetic socket is first placed over the patient's residual limb using, e.g., only one hand. With the patient's residual limb in the prosthetic socket, the same hand used to place the patient's residual limb within the opening of the prosthetic socket can be used to adjust the prosthetic socket as the prosthesis has now been sufficiently supported, e.g., on a floor. A first rotation of the adjustment disk about the first rotational axis 84 with respect to the first base 12 in a first direction causes the opening to be sufficiently enlarged to receive the patient's residual limb 44. A second rotation of the adjustment disk 40 about in a first rotational axis 84 with respect to the first base 12 in a second direction opposite the first direction, causes the opening to contract and the plurality of panels 10 to come in contact with and be tightened around the patient's residual limb and the selective locking mechanism 52 to be disposed in an on state to immobilize the plurality of panels 10 with respect to the patient's residual limb 44. To release this lock, a rotation of the outer ring 42 causes the lock-releasing mechanism to release the selective locking mechanism 52 to be disposed in an off state to allow an adjustment of the opening.

Figure 14:
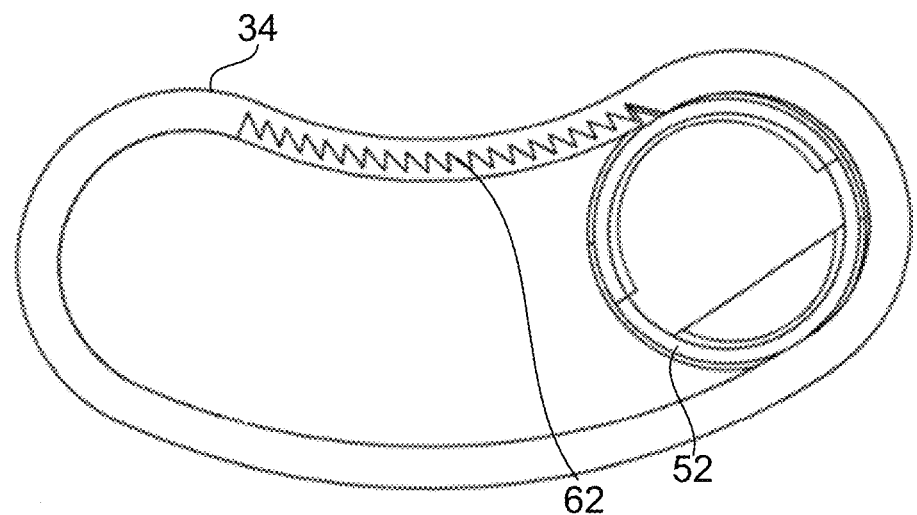
FIG. 14 is a view of a slot of a present prosthetic socket, depicting a selective locking mechanism disposed in a locked state while the present prosthetic socket is disposed at a limit in its retracted state.
Figure 15:
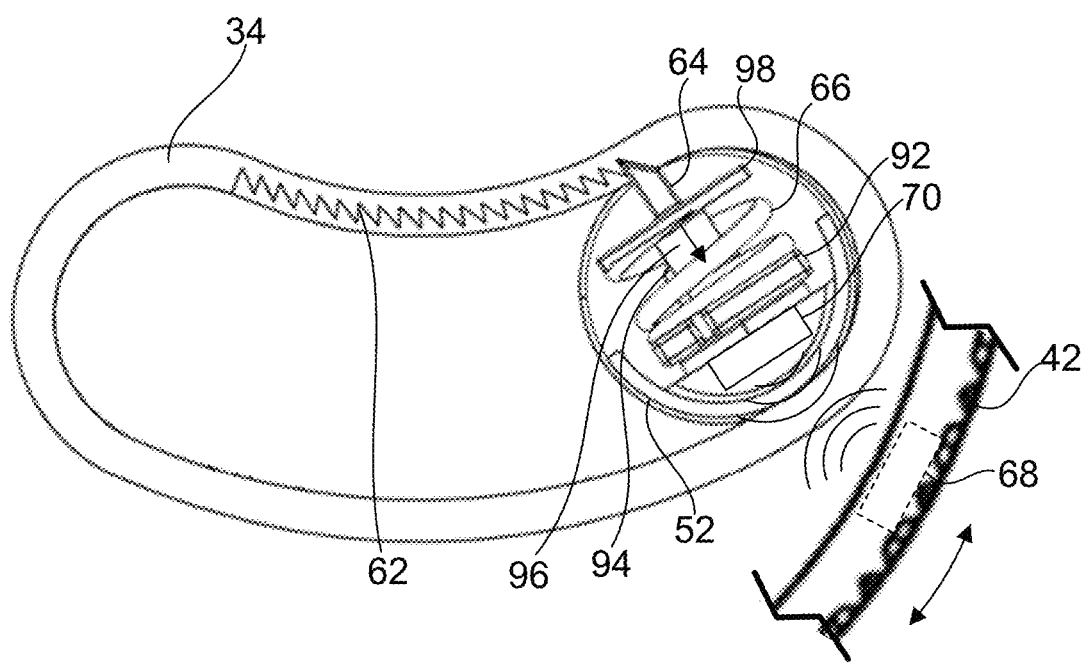
FIG. 15 is a view of FIG. 14 with a cover of the selective locking mechanism removed to reveal the interior of the selective locking mechanism.
Figure 16:
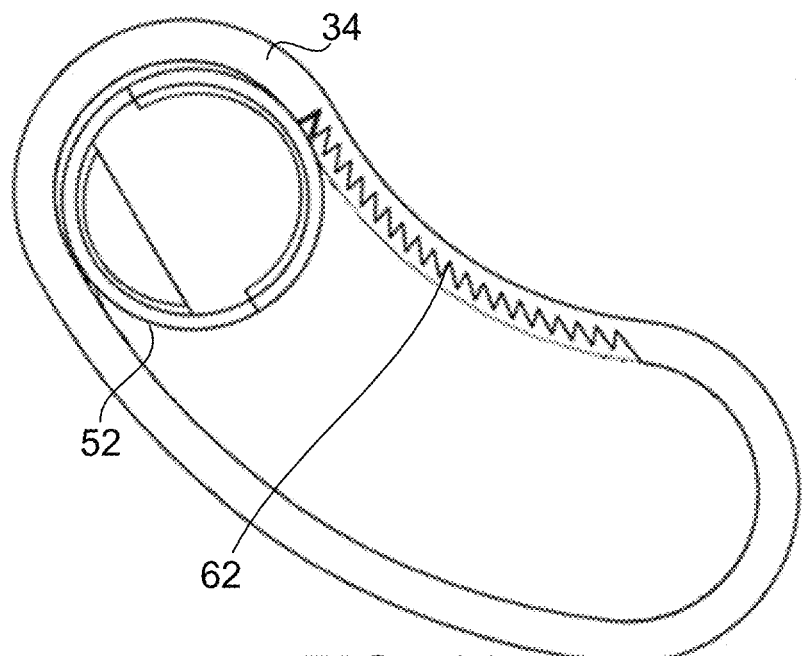
FIG. 16 is a view of a slot of a present prosthetic socket, depicting a selective locking mechanism disposed in a locked state while the present prosthetic socket is disposed at a limit in its expanded state.
Figure 17:
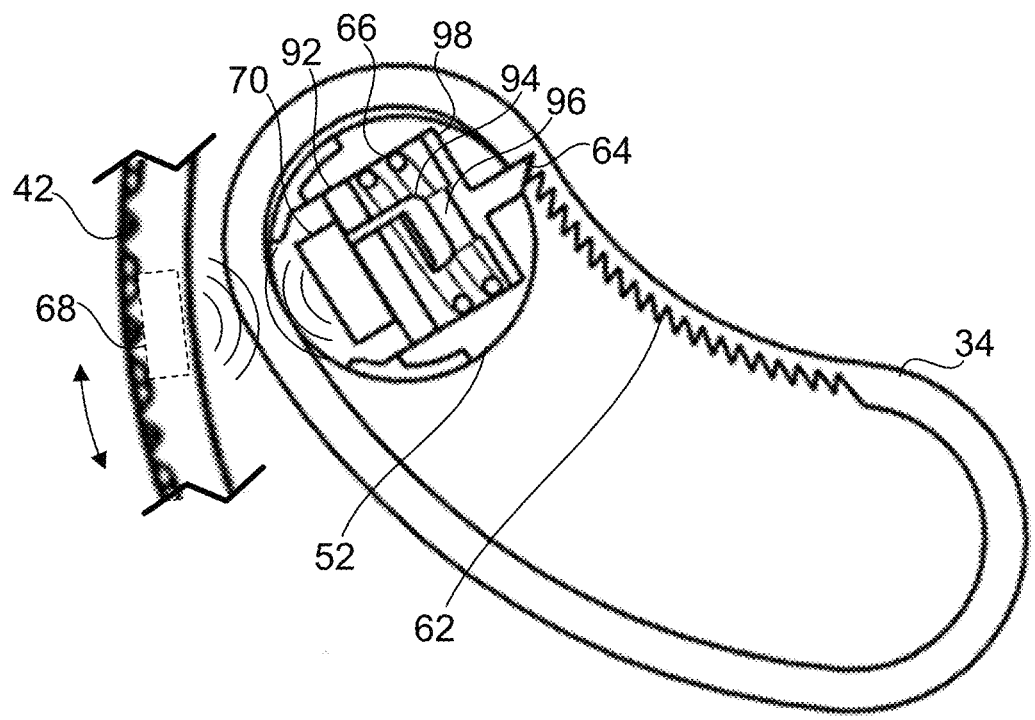
FIG. 17 is a view of FIG. 16 with a cover of the selective locking mechanism removed to reveal the interior of the selective locking mechanism.

FIG. 14 is a view of a slot 34 of a present prosthetic socket, depicting a selective locking mechanism disposed in a locked state while the present prosthetic socket is disposed at a limit in its retracted state. FIG. 15 is a view of FIG. 14 with a cover of the selective locking mechanism 52 removed to reveal the interior of the selective locking mechanism 52. FIG. 16 is a view of a slot of a present prosthetic socket, depicting a selective locking mechanism 52 disposed in a locked state while the present prosthetic socket is disposed at a limit in its expanded state. FIG. 17 is a view of FIG. 16 with a cover of the selective locking mechanism 52 removed to reveal the interior of the selective locking mechanism 52. It shall be noted that each selective locking mechanism 52 includes a rachet. The rachet includes a pawl 64 disposed in the selective locking mechanism 52 and a plurality of teeth 62 disposed along a periphery of each slot 34. Each selective locking mechanism 52 includes a first magnet 70. The adjustment disk 40 can be locked or immobilized simply by turning the adjustment disk 40 in a direction to tighten the prosthetic socket against the patient's residual limb due to the rachets. Therefore, the selective locking mechanisms 52 may be locked against the slots 34 while disposed in any position relative to the slots 34. While disposed in an on state, the selective locking mechanism 52 includes a pawl 64 disposed on one end of a spring 66, that is urged by the spring 66 to be lodged in one of the teeth 62, immobilizing the selective locking mechanism 52 with respect to the slot 34 in the direction in which the prosthetic socket expands. When a second magnet 68 disposed on the outer ring 42 comes within the magnetic field of the first magnet 70, e.g., by rotating the adjustment disk 40, the second magnet 68, which is disposed at the opposite polarity, attracts the first magnet 70, causing the first magnet 70 to move closer to the second magnet 68, retracting a hook 94 coupled with a ring 96 which extends into a plate 98 and the pawl 64, dislodging the pawl 64 from the teeth 62 to free the selective locking mechanism 52 from the slot 34. Here, the magnets 68 and 70 are arranged so that as they approach each other, their opposite polarities cause them to attract. While disposed in an off state, the selective locking mechanism 52 allows adjustment to be made of the adjustment disk with respect to the first base 12. The first magnets 70 are disposed on an interior surface of the outer ring 42 such that each of them interacts with a second magnet 68 to free the adjustment disk 40 simultaneously. Here, as the slots 34 are disposed symmetrically about the first rotational axis 84, the second magnets 68 are also disposed symmetrically about the outer ring 42. Compression of the spring 66 at a first end of the spring 66 at plate 98 and a second end of the spring 66 at a spring stop 92 fixedly attached to the selective locking mechanism 52, is sustained until the magnetic pull between the magnets 68, 70 becomes too weak when these magnets have been sufficiently distanced as the outer ring 42 continues to be rotated. It shall be noted then that, in this embodiment, a pawl 64 will re-engage with a slot once the magnetic pull ceases to be effective and the spring compression has been relieved.

Figure 18:
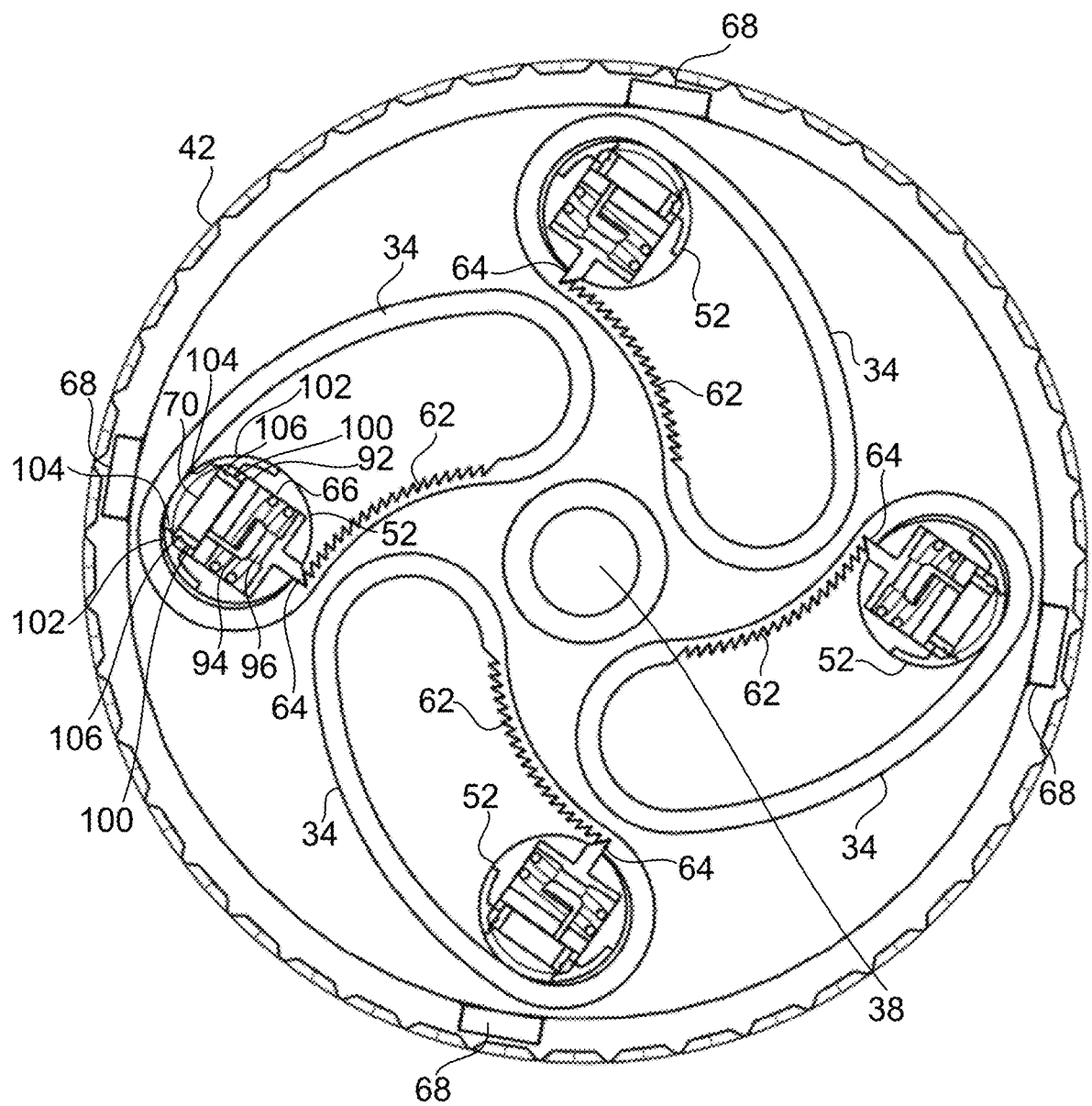
FIG. 18 is a diagram depicting another embodiment of a plurality of selective locking mechanisms of a present prosthetic socket disposed in an on state.
Figure 19:
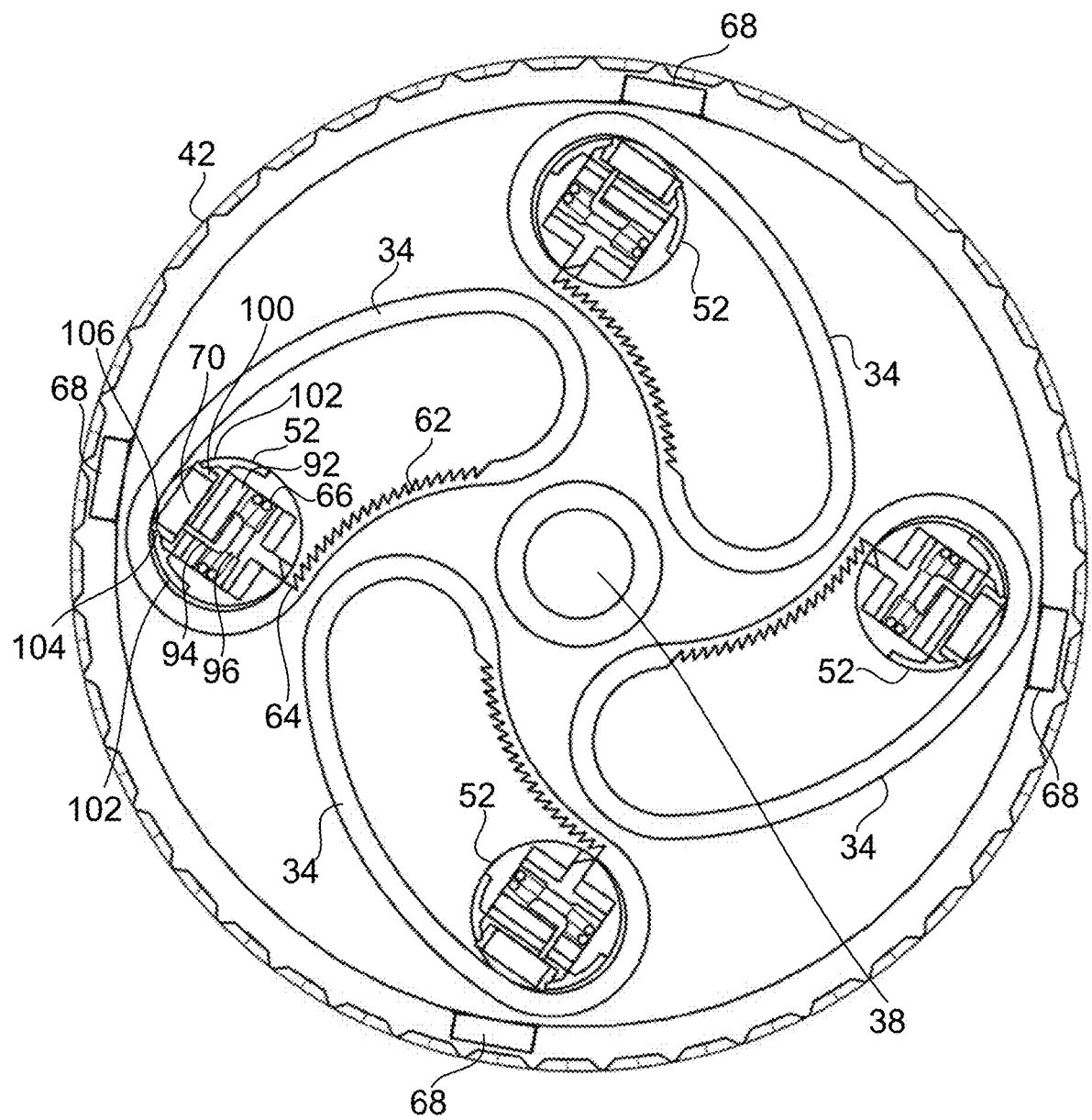
FIG. 19 is a diagram depicting the embodiment of a plurality of selective locking mechanisms of FIG. 18 disposed in an off state.
Figure 20:
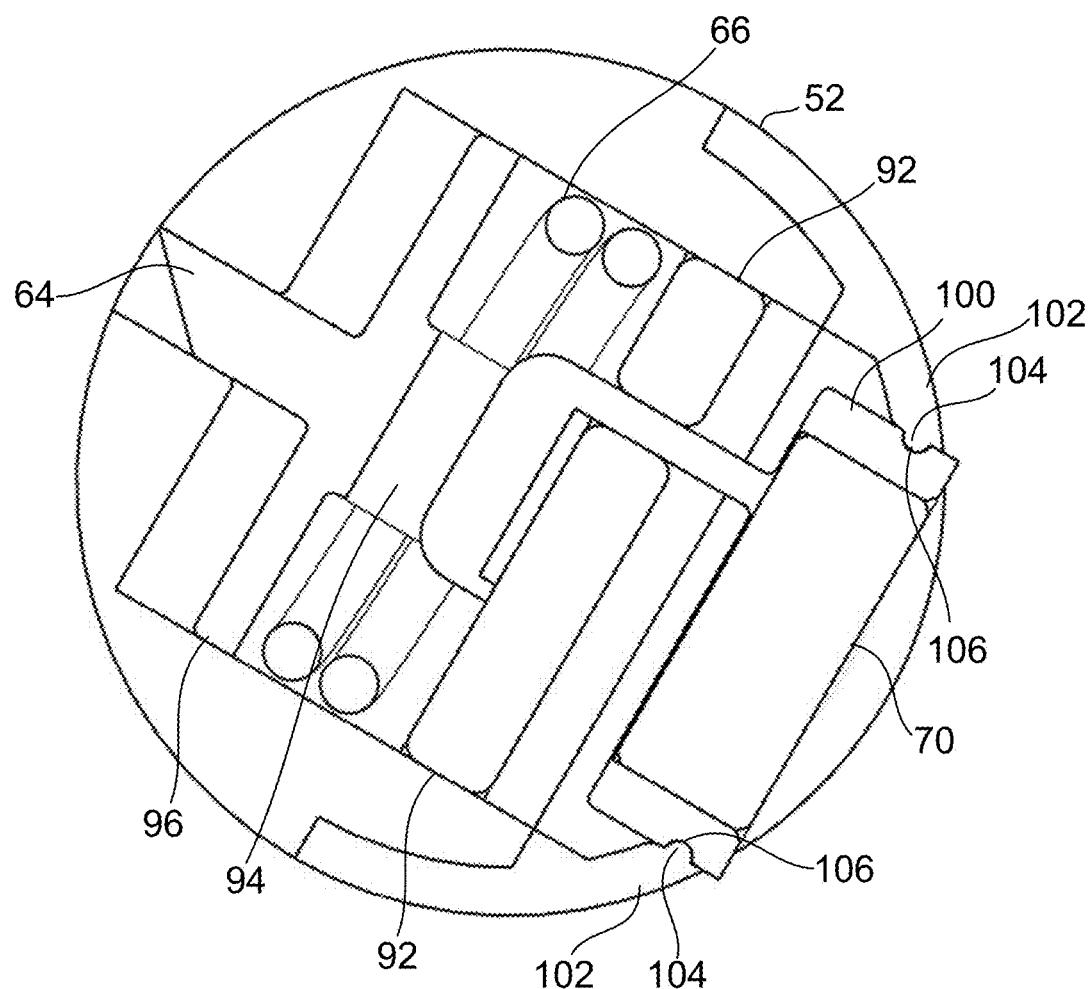
FIG. 20 is a close-up cross-sectional view of a selective locking mechanism of FIG. 18 disposed in an on state.
Figure 21:
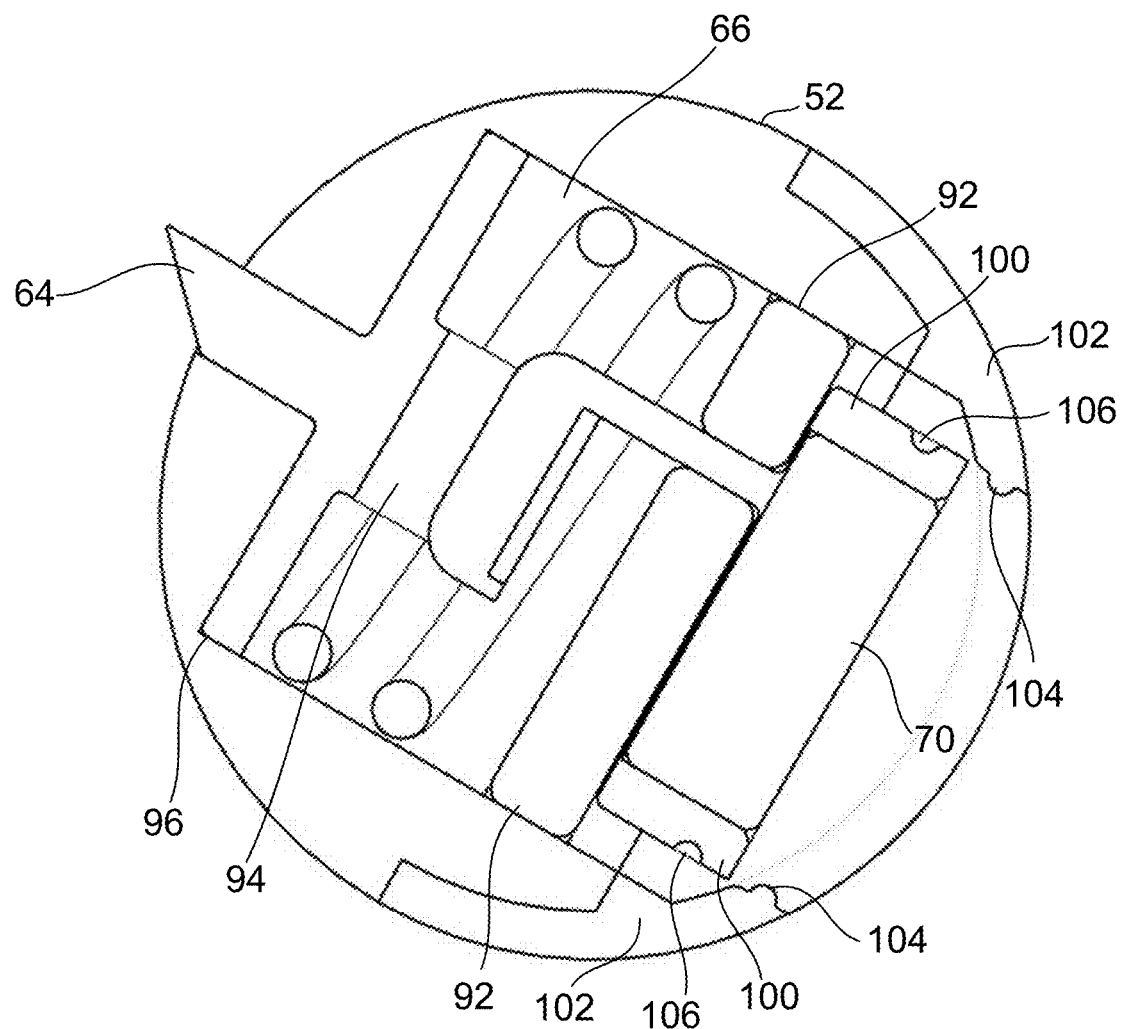
FIG. 21 is a close-up cross-sectional view of a selective locking mechanism of FIG. 18 disposed in an off state.

FIG. 18 is a diagram depicting a plurality of selective locking mechanisms 52 of a present prosthetic socket disposed in an on state. FIG. 19 is a diagram depicting the embodiment of a plurality of selective locking mechanisms 52 of FIG. 18 disposed in an off state. FIG. 20 is a close-up cross-sectional view of a selective locking mechanism 52 of FIG. 18 disposed in an on state. FIG. 21 is a close-up cross-sectional view of a selective locking mechanism 52 of FIG. 18 disposed in an off state. Here, a first magnet 70 which causes a pawl 64 to be withdrawn from the teeth 62 of a slot 34, is retained in a position to leave the pawl 64 clear of the teeth 62 after a second magnet 68, having the opposite polarity to the first magnet 70, has approached the first magnet 70 to attract the first magnet 70. It shall be noted that, in this embodiment, a housing 100 is fixedly disposed around a first magnet 70 and it is configured to be slidable with respect to a sleeve 102. Each housing-sleeve pair provides surfaces upon which snap-fit features, e.g., flexible knobs 104 configured to be snapped into divots 106, may be disposed. Here, as a first magnet 70 is attracted to a second magnet 68, flexible knobs 104 are drawn closer to their respective divots 106 and snapped in place to temporarily hold the housing 100 and sleeve 102 together. Unlike the arrangements shown in FIGS. 14-17, the polarity of the first magnets 70, is alternated about the second rotational axis 86 and the polarity of the second magnets 68, is alternated about the second rotational axis 86 as well. As the outer ring 42 continues to be rotated about the second rotational axis 86, the next pair of magnets 68, 70 enter each other's magnetic field and begin to interact. Here, all four pairs of the interacting magnets 68, 70 are now disposed at the same polarity, e.g., North-North or South-South. As magnets 68, 70 having the same polarity repel one another, the knobs 104 of each first magnet 70 then dislodge from the divots 106, causing the springs to expand to allow the respective pawls 64 to engage with their respective sets of teeth 62. It shall now be clear that, in the embodiment shown in FIGS. 18-19, the state (on or off) of each selective locking mechanism 52 may be controlled more definitively compared to the embodiment shown in FIGS. 14-17 as the pawls 64 or selective locking mechanisms 52 are retained in their off-state until the next set of magnets 68, 70 interact with one another.

Figure 22:
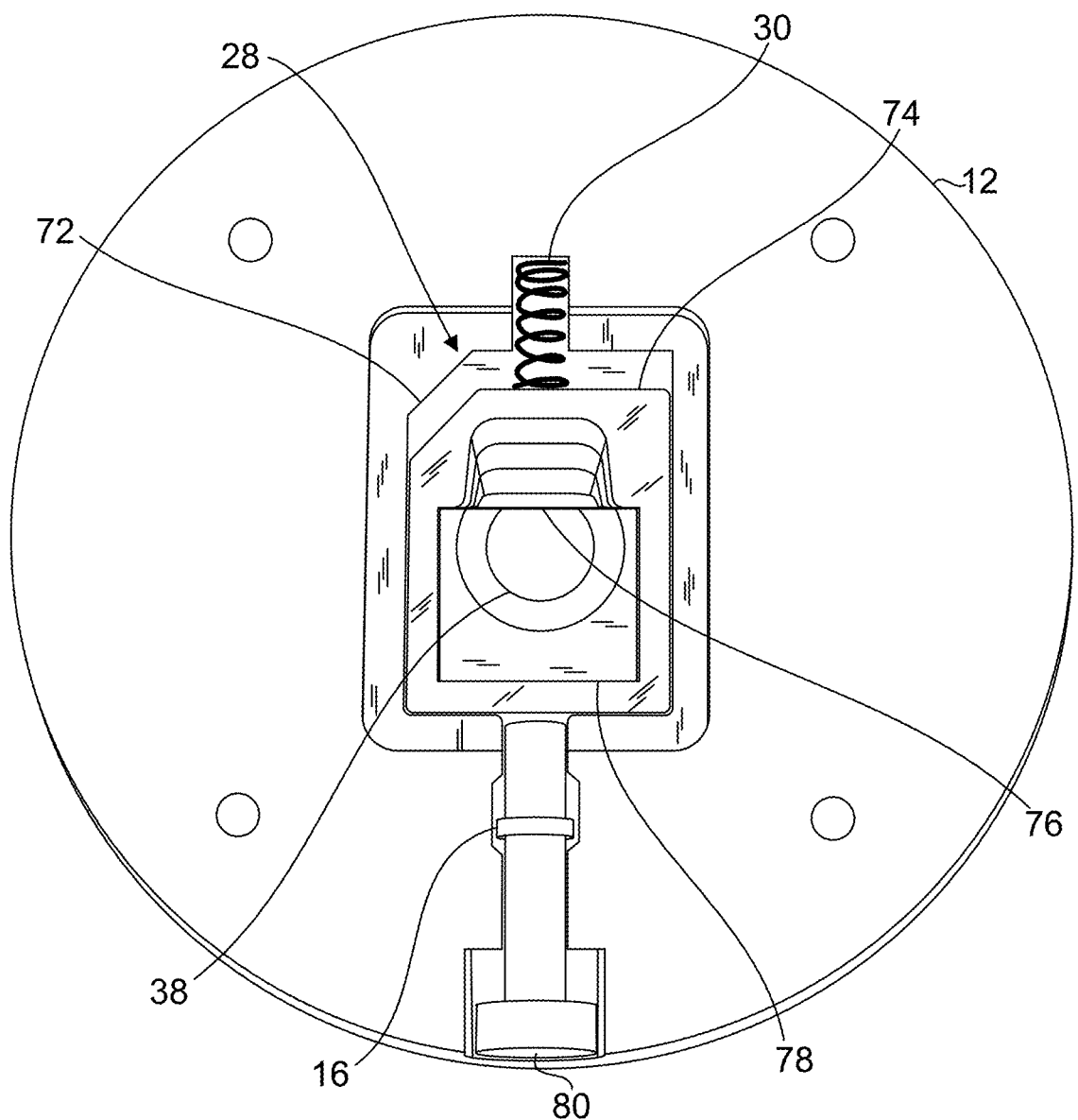
FIG. 22 is a top view of a pin lock system integrated in a present prosthetic socket, depicting the lock in a locked position.
Figure 23:
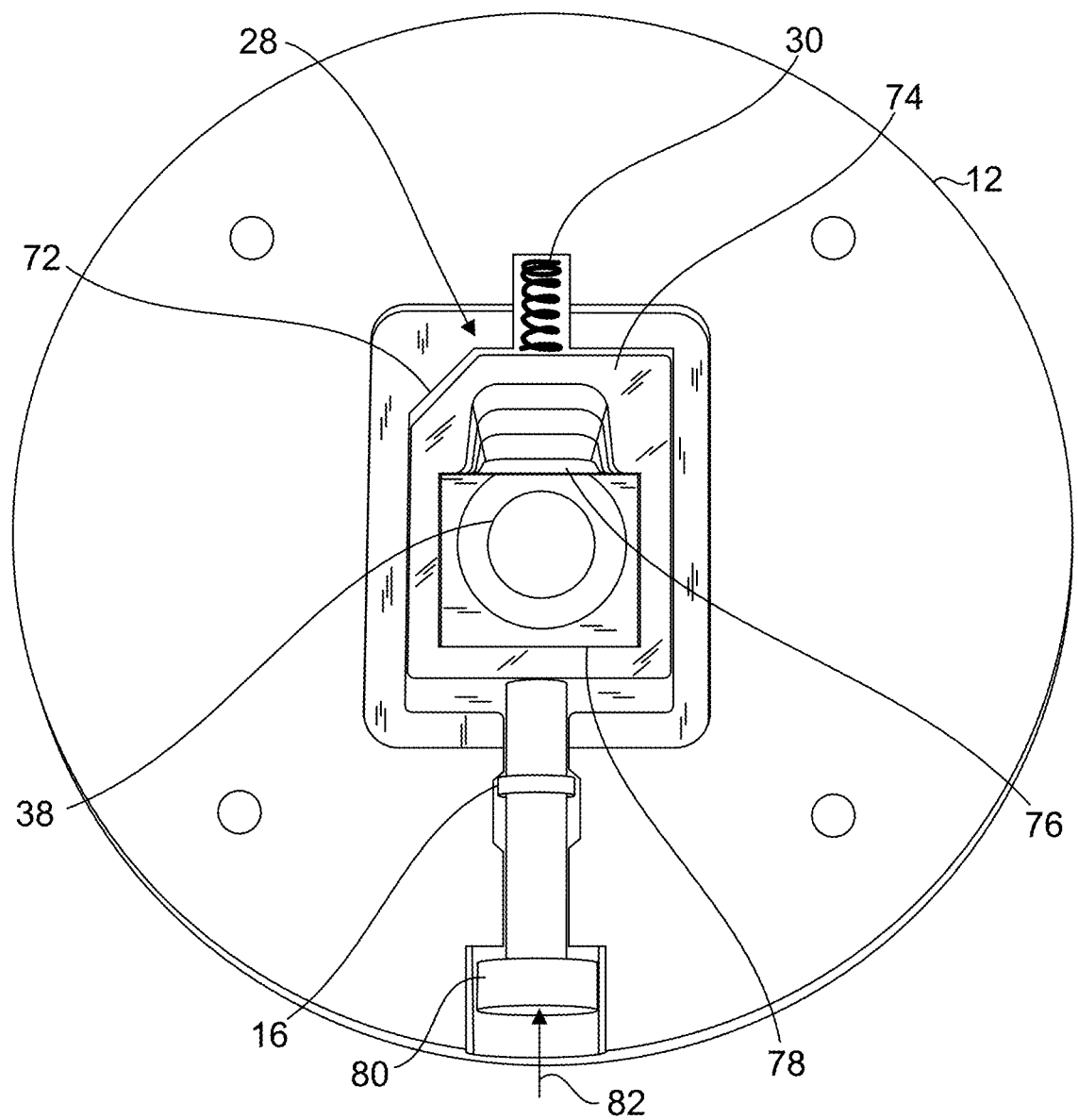
FIG. 23 is a top view of a pin lock system integrated in a present prosthetic socket, depicting the lock in an unlocked position.

FIG. 22 is a top view of a pin lock system integrated in a present prosthetic socket, depicting a lock of the pin lock system disposed in a locked position. FIG. 23 is a top view of a pin lock system integrated in a present prosthetic socket, depicting a lock of the pin lock system disposed in an unlocked position. Referring back to FIG. 4, the pin 32 of a prosthetic liner 36 is disposed through the through hole 38 before being removably immobilized with a pin lock system 28. The through hole 38 extends from the first base 12 as a connector 88 through the adjustment disk 40 before being removably connected to the second base 14, e.g., with screw threads. The second base 14 serves as a base upon which another part of the prosthesis 2, e.g., a pylon 4, is attached. In practice, a patient may secure the pin 32 of a liner 36 simply by disposing the pin 32 of a liner 36 in the through hole 38 until the pin 32 comes in contact with a tapered edge 76 of a frame 74 disposed within a cavity outlined by an outer periphery 72, to cause the frame to move in a direction such that the opening 78 of the frame 74 clears the through hole 38 while compressing a spring 30 which urges the tapered edge 76 against the pin 32 to assist in holding the pin 32 in place relative to the pin lock system 28. Referring to FIGS. 2 and 22-23, to facilitate the release of the pin 32 from the pin lock system 28, a push pin 80 is disposed on a surface of the first base 12, conveniently accessible to a user. A force may be applied using one's finger in direction 82 to move the frame 74 in a direction such that the opening 78 of the frame 74 clears the through hole 38 while compressing a spring 30 to allow the pin 32 to be removed with significantly less effort. A stop ring 16 disposed on the push pin 80 prevents overexertion of the applied force.

The detailed description refers to the accompanying drawings that show, by way of illustration, specific aspects and embodiments in which the present disclosed embodiments may be practiced. These embodiments are described in sufficient detail to enable those skilled in the art to practice aspects of the present invention. Other embodiments may be utilized, and changes may be made without departing from the scope of the disclosed embodiments. The various embodiments can be combined with one or more other embodiments to form new embodiments. The detailed description is, therefore, not to be taken in a limiting sense, and the scope of the present invention is defined only by the appended claims, with the full scope of equivalents to which they may be entitled. It will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments and other embodiments will be apparent to those of skill in the art upon studying the above description. The scope of the present disclosed embodiments includes any other applications in which embodiments of the above structures and fabrication methods are used. The scope of the embodiments should be determined with reference to the appended claims, along with the full scope of equivalents to which such claims are entitled.

What is claimed herein is:

1. A prosthetic socket comprising:
    (a) a plurality of panels;
    (b) a first base comprising a first rotational axis and a plurality of support members disposed about said first rotational axis, wherein each of said plurality of panels is supported by a corresponding support member of said plurality of support members to define a socket opening; and
    (c) an adjustment disk comprising a second rotational axis and an actuator, wherein said second rotational axis is co-axially aligned with said first rotational axis, and the actuator is functionally coupled to said plurality of support members, the actuator comprises a selective locking mechanism and a slot, the selective locking mechanism configured to extend from one of said plurality of support members,
wherein a rotation of said adjustment disk in a first direction relative to said first base moves each of the plurality of panels to a first position at which a patient's residual limb comes in contact with at least one of the plurality of panels and a cessation in the rotation of said adjustment disk causes the selective locking mechanism to engage the slot, reducing their perpendicular distance from said first rotational axis and decreasing said socket opening and immobilizing said plurality of support members and a rotation of the adjustment disk in a second, opposite direction moves each of said plurality of panels to a second position, increasing their perpendicular distance from said first rotational axis and enlarging said socket opening.

2. The prosthetic socket of claim 1, wherein said plurality of support members are four support members.

3. The prosthetic socket of claim 1, wherein a lengthwise cross-section of at least one of said plurality of support members is a polygon.

4. A prosthetic socket comprising:
    (a) a plurality of panels;
    (b) a plurality of support members, each configured to support one of the plurality of panels;
    (c) a base comprising a first base and an adjustment disk disposed adjacent to the first base, wherein said first base comprises a first rotational axis and a plurality of channels arranged about said first rotational axis, and said adjustment disk comprises a second rotational axis co-axially aligned with said first rotational axis and a plurality of slots arranged about said second rotational axis;
    (d) at least one selective locking mechanism attached to one of said plurality of support members, said at least one selective locking mechanism configured to be disposed in one of an on state and an off state, within a plane perpendicular to the first rotational axis; and
    (e) an outer ring comprising a central plane and at least one lock-releasing mechanism, said at least one lock-releasing mechanism being functionally coupled to said at least one selective locking mechanism to enable its release, wherein said outer ring is disposed such that said central plane is substantially coplanar with said plane of said at least one selective locking mechanism,
wherein each of said plurality of support members is positioned within a corresponding channel, and each of said at least one selective locking mechanism is slidably engaged with a corresponding slot of said plurality of slots such that said plurality of panels form an opening for receiving a patient's residual limb, a rotation of said adjustment disk about said first rotational axis in a first direction enlarges said opening to accommodate the patient's residual limb, a rotation of said adjustment disk in an opposite, second direction reduces said opening, bringing said plurality of panels into contact with the patient's residual limb and said at least one selective locking mechanism is placed in said on state to immobilize said plurality of panels around the patient's residual limb, and a rotation of said outer ring activates said at least one lock-releasing mechanism, transitioning said at least one selective locking mechanism to said off state, allowing adjustment of the opening.

5. The prosthetic socket of claim 4, wherein said at least one selective locking mechanism and said plurality of slots together comprise a rachet.

6. The prosthetic socket of claim 5, wherein said rachet comprises a pawl configured to be engaged with a plurality of teeth disposed along a periphery of one of said plurality of slots.

7. The prosthetic socket of claim 4, wherein said at least one selective locking mechanism comprises a first magnet, said at least one lock releasing mechanism comprises a second magnet and said second magnet is configured to interact with said first magnet to dispose said at least one selective locking mechanism in an off-state from an on-state.

8. The prosthetic socket of claim 4, further comprising a second base configured to be removably coupled with said first base, wherein said adjustment disk is disposed between said first base and said second base.

9. The prosthetic socket of claim 6, further comprising a pin lock system for releasably securing a pin of a liner disposed over the patient's residual limb.

10. The prosthetic socket of claim 4, wherein a lengthwise cross-section of at least one of said plurality of support members is a polygon.

11. The prosthetic socket of claim 4, wherein said plurality of support members are four support members.

12. A prosthetic socket comprising:
(a) a plurality of panels;
(b) a plurality of support members, each configured to support one of the plurality of panels;
(c) a base comprising a first base and an adjustment disk disposed adjacent to the first base, wherein said first base comprises a first rotational axis and a plurality of channels arranged about said first rotational axis, and said adjustment disk comprises a second rotational axis co-axially aligned with said first rotational axis and a plurality of slots arranged about said second rotational axis;
(d) at least one selective locking mechanism attached to one of said plurality of support members, said at least one selective locking mechanism configured to be disposed in one of an on state and an off state, within a plane perpendicular to the first rotational axis and said at least one selective locking mechanism and said plurality of slots together comprise a rachet; and
(e) an outer ring comprising a central plane and at least one lock-releasing mechanism, said at least one lock-releasing mechanism being functionally coupled to said at least one selective locking mechanism to enable its release, wherein said outer ring is disposed such that said central plane is substantially coplanar with said plane of said at least one selective locking mechanism, wherein each of said plurality of support members is positioned within a corresponding channel, and each of said at least one selective locking mechanism is slidably engaged with a corresponding slot of said plurality of slots such that said plurality of panels form an opening for receiving a patient's residual limb, a rotation of said adjustment disk about said first rotational axis in a first direction enlarges said opening to accommodate the patient's residual limb, a rotation of said adjustment disk in an opposite, second direction reduces said opening, bringing said plurality of panels into contact with the patient's residual limb and said at least one selective locking mechanism is placed in said on state to immobilize said plurality of panels around the patient's residual limb, and a rotation of said outer ring activates said at least one lock-releasing mechanism, transitioning said at least one selective locking mechanism to said off state, allowing adjustment of the opening.

13. The prosthetic socket of claim 12, wherein said rachet comprises a pawl configured to be engaged with a plurality of teeth disposed along a periphery of one of said plurality of slots.

14. The prosthetic socket of claim 12, wherein said at least one selective locking mechanism comprises a first magnet, said at least one lock releasing mechanism comprises a second magnet and said second magnet is configured to interact with said first magnet to dispose said at least one selective locking mechanism in an off-state from an on-state.

15. The prosthetic socket of claim 12, further comprising a second base configured to be removably coupled with said first base, wherein said adjustment disk is disposed between said first base and said second base.

16. The prosthetic socket of claim 12, further comprising a pin lock system for releasably securing a pin of a liner disposed over the patient's residual limb.

17. The prosthetic socket of claim 12, wherein a lengthwise cross-section of at least one of said plurality of support members is a polygon.

18. The prosthetic socket of claim 12, wherein said plurality of support members are four support members.

* * * * *